United States Patent [19]

Williams et al.

[11] Patent Number: 5,589,364
[45] Date of Patent: Dec. 31, 1996

[54] RECOMBINANT PRODUCTION OF BIOLOGICALLY ACTIVE PEPTIDES AND PROTEINS

[75] Inventors: Jon I. Williams, Robbinsville, N.J.; James C. Pierce, Wilmington, Del.; G. Mark Anderson, Norristown; Prasad Kari, Lansdale, both of Pa.

[73] Assignee: Magainin Pharmaceuticals Inc., Plymouth Meeting, Pa.

[21] Appl. No.: 282,030

[22] Filed: Jul. 29, 1994

[51] Int. Cl.$^6$ ..................................................... C12P 21/00
[52] U.S. Cl. ..................... 435/69.7; 435/69.1; 435/172.3
[58] Field of Search .................................... 435/69.1, 69.7, 435/172.3; 935/38, 47

[56] References Cited

U.S. PATENT DOCUMENTS

| | | | |
|---|---|---|---|
| 5,028,530 | 7/1991 | Lai et al. | 435/69.1 |
| 5,104,796 | 4/1992 | Keith et al. | 435/69.4 |
| 5,206,154 | 4/1993 | Lai et al. | 435/69.7 |
| 5,264,365 | 11/1993 | Georgiou et al. | 435/252.8 |

FOREIGN PATENT DOCUMENTS

| | | |
|---|---|---|
| 0578472A2 | 1/1994 | European Pat. Off. . |
| WO86/04356 | 7/1986 | WIPO . |
| WO88/00976 | 2/1988 | WIPO . |
| 89/02465 | 3/1989 | WIPO . |
| WO89/04371 | 5/1989 | WIPO . |
| WO93/24513 | 12/1993 | WIPO . |
| WO93/24138 | 12/1993 | WIPO . |
| WO94/04688 | 3/1994 | WIPO . |
| WO94/09810 | 5/1994 | WIPO . |

OTHER PUBLICATIONS

Baneyx, F., et al. (1992) Ann. N. Y. Acad Sci. 665, 301–308.
K. Venema et al., "Mode of Action of LciA, the Lactococcin A Immunity Protein," *Molecular Microbiology*, 1994, pp. 521–532.
S. Taguchi et al., "Extracellular Production System of Heterologous Peptide Driven by a Secretory Protease Inhibitor of *Streptomyces*," *Appl. Microbiol Biotechnol.*, 1992, pp. 749–753.
D. Alexander et al., "Isolation and Purification of a Biologically Active Human Platelet–Derived Growth Factor BB Expressed in *Escherichia coli*," *Protein Expression and Purification*, 1992, pp. 204–211.
N. Cardenas et al., "Expression and Characterization of Recombinant mts–1 Protein" (CA Abstract Only) from Bioorg. Khim. (1993) 19(4), pp. 420–426.
Ohta et al.; Mechanisms of Antibacterial Action of Tachyplesins and Poly–phemusins, a Group of Antimicrobial Peptides Isolated from Horseshoe Crab Hemocytes; Antimicrobial Agents and Chemotherapy; vol. 36, No. 7; Jul. 1992; pp. 1460–1465.
Grodberg et al.; ompT Encodes the *Escherichia coli* Outer Membrane Protease That Cleaves T7 RNA Polymerase during Purification; Journal of Bacteriology; vol. 170, No. 3; Mar. 1988; pp. 1245–1253.

Hussain et al.; Expression of ricin B chain in *Escherichia coli*; FEBS Letters; vol. 244, No. 2; Feb. 1989; pp. 383–387.
Richardson et al.; The expression of functional ricin B–chain in *Saccharomyces cerevisiae*; Biochimica et Biophysica Acta. 950; 1988; pp. 385–394.
Handl et al; High Yield of Active STb Enterotoxin from a Fusion Protein (MBP–STb) Expressed in *Escherichia coli*; Protein Expression and Purification 4; 1993; pp. 275–281.
Bedouelle et al.; Production in *Escherichia coli* and one–step purification of bifunctional hybrid proteins which bind maltose; Eur. J. Biochem. 171; 1988; pp. 541–549.
Martineau et al.; Expression of heterologous peptides at two permissive sites of the MalE protein: antigenicity and immunogenicity of foreign B–cell and T–cell epitopes; Gene, 113; 1992; pp. 35–46.
Clement et al.; Bacterial vectors to target and/or purify polypeptides; their use in immunological studies; Ann. Biol. Clin., 49; 1991; pp. 249–254.
Szmelcman etal.; Export and One–Step Purification from *Escherichia coli* of a MalE–CD4 Hybrid Protein That Neutralizes HIV In Vitro; Journal of Acquired Immune Deficiency Syndromes, 3; 1990; pp. 859–872.
di Guan et al.; Vectors that facilitate the expression and purification of foreign peptides in *Escherichia coli* by fusion to maltose–binding protein; Gene, 67; 1988; pp. 21–30.
Blondel et al.; Export and purifiction of a cytoplasmic dimeric protein by fusion to the maltose–binding protein of *Escherichia coli*; Eur. J. Biochem. 193; 1990; pp. 325–330.
Protein Fusion & Purification System Instruction Manual; New England BioLabs; Version 3.01; Revised 2/93, pp. 1–37.

(List continued on next page.)

Primary Examiner—Charles L. Patterson, Jr.
Attorney, Agent, or Firm—Finnegan, Henderson, Farabow, Garrett & Dunner, L.L.P.

[57] ABSTRACT

The present invention relates to the recombinant production of amphiphilic peptides with biologically and therapeutically significant activities. In one embodiment, this invention relates to recombinantly producing an amphiphilic peptide by providing a protease-deficient microbial host transformed with an expression vector containing DNA that encodes the amphiphilic peptide under the control of a regulatory sequence operable in the microbial host and expressing the amphiphilic peptide in the transformed microbial host. In another embodiment, this invention relates to providing an *E. coli* protease-deficient K-12 cell transformed with a vector that expresses a cleavable fusion protein comprising at least part of a carbohydrate binding protein and the amphiphilic peptide in the cell, expressing the fusion protein in the cell, and cleaving the fusion protein to obtain the amphiphilic peptide substantially free of carbohydrate binding protein residues. The biologically active amphiphilic peptide so produced can be further treated chemically or enzymatically to obtain a chemically distinct amphiphilic peptide with improved biological and therapeutic properties.

39 Claims, 2 Drawing Sheets

OTHER PUBLICATIONS

Casteels–Josson et al.; Apidaecin multipeptide precursor structure; a putative mechanism for amplication of the insect antibacterial response; The EMBO Journal, vol. 12, No. 4; 1993; pp. 1569–1578.

Elish et al.; Biochemical Analysis of Spontaneous fepA Mutants of *Escherichia coli* Journal of General Microbiology, vol. 134; 1988; pp. 1355–1364.

Iwanaga; Primitive Coagulation Systems and their Message to Modern Biology; Thrombosis and Haemostasis; 70(1); 1993; pp. 48–55.

Kokryakov et al.; Protegrins: leukocyte antimicrobial peptides that combine features of cortiscostatic defensins and tachyplesins; FEBS Letters; vol. 327, No. 2; Jul. 1993; pp. 231–136.

Lama et al.; Expression of Poliovirus Nonstructural Proteins in *Escherichai coli* Cells; The Journal of Biological Chemistry; vol. 267, No. 22; Aug. 5, 1992; pp. 15932–15937.

Hellers et al., Expression and post–translational processing of preprocecropin A using a baculovirus vector; European Journal of Biochemistry; vol. 199; 1991; pp. 435–439.

Gunne etal.; Structure of preproattacin and its processing in insect cells infected with a recombinant baculovirus; European Journal of Biochemistry; vol. 187; 1990; pp. 699–703.

Lama et al.; Inducible expression of a toxic poliovirus membrane protein in *Escherichia coli*: Comparative studies using different expression systems based on T7 promoters; Biochemical and Biophysical Research Communications; vol. 188, No. 3; 1992; pp. 972–981.

Yee et al.; Recombinant protein expression in high cell density fed–batch cultures of *Escherichia coli*; Biotechnology, vol. 10; Dec. 1992; pp. 1550–1556.

Yee et al.; Recombinant Trypsin Production in High Cell Density Fed–Batch Cultures in *Escherichia coli*; Biotechnology and Bioengineering vol. 47; 1993; pp. 781–790.

Wales et al.; Mutational Analysis of the Galactose Binding Ability of Recombinant Ricin B Chain; The Journal of Biological Chemistry vol. 266, vol. 29; Oct. 15, 1991; pp. 19172–19279.

Qoronfleh et al.; A Modified pET Vector that Augments Heterologous Protein Expression; Biotechnology Letters, vol. 15, No. 4; Apr. 1993; pp. 337–340.

Piers et al.; Recombinant DNA procedures for producing small anti–microbial cationic peptides in bacteria; Gene, vol. 134; 1993; pp. 7–13.

Bibi et al.; Functional expression of mouse mdr1 in *Escherichia coli*; Proc. Natl. Acad. Sci., vol. 90; Oct. 1993; pp. 9209–9213.

Sugimura et al.; Purification, Characterization, and Primary Structure Residues: Identity of Protease VII and OmpT; Journal of Bacteriology vol. 170, No. 12; Dec. 1988; pp. 5625–5632.

McIntosh et al.; Genetic and Physiological Studies on the Relationship Between Colicin B Resistance and Ferrienterochelin Uptake in *Escherichia coli* K–12; Journal of Bacteriology, vol. 137, No. 1; Jan. 1979; pp. 653–657.

Schein; Production of Soluble Recombinant Proteins in Bacteria; Biotechnology, vol. 7; Nov. 1989; pp. 1141–1149.

SEQUENCE LISTING ( 1 ) GENERAL INFORMATION:

( i i i ) NUMBER OF SEQUENCES: 62

( 2 ) INFORMATION FOR SEQ ID NO:1:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Ser Trp Leu Ser Lys Thr Ala Lys Lys Leu Glu Asn Ser Ala Lys Lys
 1               5                  10                      15

Arg Ile Ser Glu Gly Ile Ala Ile Ala Ile Gln Gly Gly Pro Arg
             20                  25                  30
```

( 2 ) INFORMATION FOR SEQ ID NO:2:

( i ) SEQUENCE CHARACTERISTICS:
        ( A ) LENGTH: 21 amino acids (B) TYPE: amino acid
(D) TOPOLOGY: linear (ii) MOLECULE TYPE: peptide (xi) SEQUENCE DESCRIPTION: SEQ ID NO:2:

| Lys | Ile | Ala | Gly | Lys | Ile | Ala | Lys | Ile | Ala | Gly | Lys | Ile | Ala | Lys | Ile |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ala | Gly | Lys | Ile | Ala |
|-----|-----|-----|-----|-----|
|     |     |     | 20  |     |

(2) INFORMATION FOR SEQ ID NO:3:

(i) SEQUENCE CHARACTERISTICS:
   (A) LENGTH: 38 amino acids
   (B) TYPE: amino acid
   (D) TOPOLOGY: linear (ii) MOLECULE TYPE: peptide (xi) SEQUENCE DESCRIPTION: SEQ ID NO:3:

| Lys | Trp | Lys | Leu | Phe | Lys | Lys | Ile | Glu | Lys | Val | Gly | Gln | Asn | Ile | Arg |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Asp | Gly | Ile | Ile | Lys | Ala | Gly | Pro | Ala | Val | Ala | Val | Val | Gly | Gln | Ala |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Thr | Gln | Ile | Ala | Lys | Gly |
|-----|-----|-----|-----|-----|-----|
|     |     | 35  |     |     |     |

(2) INFORMATION FOR SEQ ID NO:4:

(i) SEQUENCE CHARACTERISTICS:
   (A) LENGTH: 22 amino acids
   (B) TYPE: amino acid
   (D) TOPOLOGY: linear (ii) MOLECULE TYPE: peptide (xi) SEQUENCE DESCRIPTION: SEQ ID NO:4:

| Gly | Ile | Gly | Lys | Phe | Leu | Lys | Lys | Ala | Lys | Lys | Phe | Gly | Lys | Ala | Phe |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Val | Lys | Ile | Leu | Lys | Lys |
|-----|-----|-----|-----|-----|-----|
|     |     |     | 20  |     |     |

(2) INFORMATION FOR SEQ ID NO:5:

(i) SEQUENCE CHARACTERISTICS:
   (A) LENGTH: 14 amino acids
   (B) TYPE: amino acid
   (D) TOPOLOGY: linear (ii) MOLECULE TYPE: peptide (xi) SEQUENCE DESCRIPTION: SEQ ID NO:5:

| Lys | Lys | Leu | Leu | Lys | Lys | Leu | Lys | Lys | Leu | Leu | Lys | Lys | Leu |
|-----|-----|-----|-----|-----|-----|-----|-----|-----|-----|-----|-----|-----|-----|
| 1   |     |     |     | 5   |     |     |     |     | 10  |     |     |     |     |

(2) INFORMATION FOR SEQ ID NO:6:

(i) SEQUENCE CHARACTERISTICS:
   (A) LENGTH: 23 amino acids
   (B) TYPE: amino acid
   (D) TOPOLOGY: linear (ii) MOLECULE TYPE: peptide (xi) SEQUENCE DESCRIPTION: SEQ ID NO:6:

| Gly | Ile | Gly | Lys | Phe | Leu | Lys | Lys | Ala | Lys | Lys | Phe | Gly | Lys | Ala | Gly |
|-----|-----|-----|-----|-----|-----|-----|-----|-----|-----|-----|-----|-----|-----|-----|-----|

5,589,364

49                                                                                  50

-continued

```
                1              5                    10                   15
        Val  Lys  Ile  Leu  Lys  Lys  Gly
                              20
```

( 2 ) INFORMATION FOR SEQ ID NO:7:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

```
        Arg  Arg  Trp  Cys  Phe  Arg  Val  Cys  Tyr  Arg  Gly  Phe  Cys  Tyr  Arg  Lys
        1                   5                        10                       15
        Cys  Arg
```

( 2 ) INFORMATION FOR SEQ ID NO:8:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

```
        Arg  Arg  Trp  Cys  Phe  Arg  Val  Cys  Tyr  Arg  Gly  Phe  Cys  Tyr  Arg  Lys
        1                   5                        10                       15
        Cys  Arg  Gly
```

( 2 ) INFORMATION FOR SEQ ID NO:9:

( i ) SEQUENCE CHARACTERISTICS:
        ( A ) LENGTH: 23 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

```
        Gly  Ile  Gly  Lys  Phe  Leu  His  Ser  Ala  Lys  Lys  Phe  Gly  Lys  Ala  Phe
        1                   5                        10                       15
        Val  Gly  Glu  Ile  Met  Asn  Ser
                              20
```

( 2 ) INFORMATION FOR SEQ ID NO:10:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

```
        Ala  Cys  Tyr  Cys  Arg  Ile  Pro  Ala  Cys  Ile  Ala  Gly  Glu  Arg  Arg  Tyr
        1                   5                        10                       15
        Gly  Thr  Cys  Ile  Tyr  Gln  Gly  Arg  Leu  Trp  Ala  Phe  Cys  Cys
                              20                   25                       30
```

( 2 ) INFORMATION FOR SEQ ID NO:11:

( i ) SEQUENCE CHARACTERISTICS:
        ( A ) LENGTH: 35 amino acids ( B ) TYPE: amino acid
( D ) TOPOLOGY: linear ( i i ) MOLECULE TYPE: peptide ( x i ) SEQUENCE DESCRIPTION: SEQ ID NO:11:

Gln Ala Arg Ala Thr Cys Tyr Cys Arg Thr Gly Arg Cys Ala Thr Arg
1               5                   10                  15

Glu Ser Leu Ser Gly Val Cys Glu Ile Ser Gly Arg Arg Tyr Arg Leu
            20              25                  30

Cys Cys Arg
        35

( 2 ) INFORMATION FOR SEQ ID NO:12:

( i ) SEQUENCE CHARACTERISTICS:
( A ) LENGTH: 44 base pairs
( B ) TYPE: nucleic acid
( C ) STRANDEDNESS: single
( D ) TOPOLOGY: linear ( x i ) SEQUENCE DESCRIPTION: SEQ ID NO:12:

CTTATTAGCG CGGGCCACCC TGAATAGCGA TTGCGATACC TTCA          44

( 2 ) INFORMATION FOR SEQ ID NO:13:

( i ) SEQUENCE CHARACTERISTICS:
( A ) LENGTH: 53 base pairs
( B ) TYPE: nucleic acid
( C ) STRANDEDNESS: single
( D ) TOPOLOGY: linear ( x i ) SEQUENCE DESCRIPTION: SEQ ID NO:13:

AATTCATGTC CTGGCTGTCT AAAACTGCTA AGAAACTGGA AAACTCCGCT AAA          53

( 2 ) INFORMATION FOR SEQ ID NO:14:

( i ) SEQUENCE CHARACTERISTICS:
( A ) LENGTH: 59 base pairs
( B ) TYPE: nucleic acid
( C ) STRANDEDNESS: single
( D ) TOPOLOGY: linear ( x i ) SEQUENCE DESCRIPTION: SEQ ID NO:14:

AAACGCATCT CTGAAGGTAT CGCAATCGCT ATTCAGGGTG GCCCGCGCTA ATAAGTGCA          59

( 2 ) INFORMATION FOR SEQ ID NO:15:

( i ) SEQUENCE CHARACTERISTICS:
( A ) LENGTH: 60 base pairs
( B ) TYPE: nucleic acid
( C ) STRANDEDNESS: single
( D ) TOPOLOGY: linear ( x i ) SEQUENCE DESCRIPTION: SEQ ID NO:15:

GAGATGCGTT TTTTAGCGGA GTTTTCCAGT TTCTTAGCAG TTTTAGACAG CCAGGACATG          60

( 2 ) INFORMATION FOR SEQ ID NO:16:

( i ) SEQUENCE CHARACTERISTICS:
( A ) LENGTH: 115 base pairs
( B ) TYPE: nucleic acid
( C ) STRANDEDNESS: single
( D ) TOPOLOGY: linear ( x i ) SEQUENCE DESCRIPTION: SEQ ID NO:16:

AATTCATGTC CTGGCTGTCT AAAACTGCTA AGAAACTGGA AAACTCCGCT AAAAAACGCA          60

TCTCTGAAGG GCGATTTTTT GCGTAGAGAC TTCGTGGCCC GCGCTAATAA GTGCA    115

( 2 ) INFORMATION FOR SEQ ID NO:17:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

ATGAAAATCG CTGGTAAAAT TGCAAAGATA GCAGGTAAGA TCGCGAAAAT AGCGGGCAAG    60

ATAGCTTAAT AACTGCA    77

( 2 ) INFORMATION FOR SEQ ID NO:18:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

GTTATTAAGC TATCTTGCCC GCTATTTTCG CGATCTTACC TGCTATCTTT GCAATTTTAC    60

CAGCGATTTT CAT    73

( 2 ) INFORMATION FOR SEQ ID NO:19:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

ATGAAAATCG CTGGTAAAAT TGCAAAGATA GCAGGTAAGA TCGCGAAAAT AGCGGGCAAG    60

ATAGCTTAAT AACTGCA    77

( 2 ) INFORMATION FOR SEQ ID NO:20:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

AATTCATGAA ATGGAAACTG TTCAAGAAAA TCGAGAAAGT AGGTCAGAAC ATCCGC    56

( 2 ) INFORMATION FOR SEQ ID NO:21:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

CTTATTATTT AGCGATCTGA GTAGCCTGGC CAACAACTGC TACAGCCGGA CCA    53

( 2 ) INFORMATION FOR SEQ ID NO:22:

( i ) SEQUENCE CHARACTERISTICS:
        ( A ) LENGTH: 74 base pairs
        ( B ) TYPE: nucleic acid ( C ) STRANDEDNESS: single
( D ) TOPOLOGY: linear ( x i ) SEQUENCE DESCRIPTION: SEQ ID NO:22:

GACGGTATCA TCAAAGCTGG TCCGGCTGTA GCAGTTGTTG GCCAGGCTAC TCAGATCGCT  60

AAATAATAAG TGCA  74

( 2 ) INFORMATION FOR SEQ ID NO:23:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

GCTTTGATGA TACCGTCGCG GATGTTCTGA CCTACTTTCT CGATTTTCTT GAACAGTTTC  60

CATTTCATG  69

( 2 ) INFORMATION FOR SEQ ID NO:24:

( i ) SEQUENCE CHARACTERISTICS:
        ( A ) LENGTH: 130 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

AATTCATGAA ATGGAAACTG TTCAAGAAAA TCGAGAAAGT AGGTCAGAAC ATCCGCGACG  60

GTATCATCAA AGCTGGTCCG GCTGTAGCAG TTGTTGGCCA GGCTACTCAG ATCGCTAAAT  120

AATAAGTGCA  130

( 2 ) INFORMATION FOR SEQ ID NO:25:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

AATTCATGGG TATCGGTAAA TTCCTGAAAA AAGCTAAGAA ATTCGGTAAA GCTTTCGTAA  60

AGATCCTTAA GAAATAATAA GTGCA  85

( 2 ) INFORMATION FOR SEQ ID NO:26:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

CTTATTATTT CTTAAGGATC TTTACGAAAG CTTTACCGAA TTTCTTAGCT TTTTTCAGGA  60

ATTTACCGAT ACCCATG  77

( 2 ) INFORMATION FOR SEQ ID NO:27:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

AATTCATGGG TATCGGTAAA TTCCTGAAAA AAGCTAAGAA ATTCGGTAAA GCTTTCGTAA    60

AGATCCTTAA GAAATAATAA GTGCA    85

( 2 ) INFORMATION FOR SEQ ID NO:28:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:28:

GATCGATGAA GAAACTGCTG AAAAAACTCA AAAAGCTTCT GAAAAAACTG TAATAA    56

( 2 ) INFORMATION FOR SEQ ID NO:29:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:29:

GATCTTATTA CAGTTTTTTC AGAAGCTTTT TGAGTTTTTT CAGCAGTTTC TTCATC    56

( 2 ) INFORMATION FOR SEQ ID NO:30:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

GATCGATGAA GAAACTGCTG AAAAAACTCA AAAAGCTTCT GAAAAAACTG TAATAA    56

( 2 ) INFORMATION FOR SEQ ID NO:31:

( i ) SEQUENCE CHARACTERISTICS:
        ( A ) LENGTH: 88 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

AATTCATGGG TATCGGTAAA TTCCTGAAAA AAGCTAAGAA ATTCGGTAAA GCTTTCGTAA    60

AGATCCTTAA GAAAGGTTAA TAACTGCA    88

( 2 ) INFORMATION FOR SEQ ID NO:32:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

GTTATTAACC TTTCTTAAGG ATCTTTACGA AAGCTTTACC GAATTCTTA GCTTTTTCA    60

GGAATTTACC GATACCCATG    80

( 2 ) INFORMATION FOR SEQ ID NO:33:

( i ) SEQUENCE CHARACTERISTICS:
        ( A ) LENGTH: 88 base pairs (B) TYPE: nucleic acid
(C) STRANDEDNESS: single
(D) TOPOLOGY: linear (xi) SEQUENCE DESCRIPTION: SEQ ID NO:33:

```
AATTCATGGG TATCGGTAAA TTCCTGAAAA AAGCTAAGAA ATTCGGTAAA GCTTTCGTAA    60
AGATCCTTAA GAAAGGTTAA TAACTGCA                                       88
```

(2) INFORMATION FOR SEQ ID NO:34:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO:34:

```
AATTCATGCG TCGCTGGTGT TTCCGCGTCT GCTACCGTGG CTTCTGTTAT CGTAAATGCC    60
GTTAATAACT AA                                                        72
```

(2) INFORMATION FOR SEQ ID NO:35:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO:35:

```
AGCTTAAGTT ATTAACGGCA TTTACGATAA CAGAAGCCAC GGTAGCAGAC GCGGAAACAC    60
CAGCGACGCA TG                                                        72
```

(2) INFORMATION FOR SEQ ID NO:36:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO:36:

```
AATTCATGCG TCGCTGGTGT TTCCGCGTCT GCTACCGTGG CTTCTGTTAT CGTAAATGCC    60
GTTAATAACT AA                                                        72
```

(2) INFORMATION FOR SEQ ID NO:37:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (xi) SEQUENCE DESCRIPTION: SEQ ID NO:37:

```
AATTCATGCG TCGCTGGTGT TTCCGCGTCT GCTACCGTGG CTTCTGTTAT CGTAAATGCC    60
GTGGTTAATA ACTTA                                                     75
```

(2) INFORMATION FOR SEQ ID NO:38:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (xi) SEQUENCE DESCRIPTION: SEQ ID NO:38:

```
AGCTTAAGTT ATTAACCACG GCATTTACGA TAACAGAAGC CACGGTAGCA GACGCGGAAA         60

CACCAGCGAC GCATG                                                        75
```

( 2 ) INFORMATION FOR SEQ ID NO:39:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:39:

```
AATTCATGCG TCGCTGGTGT TTCCGCGTCT GCTACCGTGG CTTCTGTTAT CGTAAATGCC         60

GTGGTTAATA ACTTA                                                        75
```

( 2 ) INFORMATION FOR SEQ ID NO:40:

( i ) SEQUENCE CHARACTERISTICS:
        ( A ) LENGTH: 88 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:40:

```
AATTCATGGG TATCGGTAAA TTCCTGCACT CCGCTAAGAA ATTCGGTAAA GCTTTCGTAG         60

GTGAAATCAT GAACTCTTAA TAAGTGCA                                          88
```

( 2 ) INFORMATION FOR SEQ ID NO:41:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:41:

```
CTTATTAAGA GTTCATGATT TCACCTACGA AAGCTTTACC GAATTTCTTA GCGGAGTGCA         60

GGAATTTACC GATACCCATG                                                   80
```

( 2 ) INFORMATION FOR SEQ ID NO:42:

( i ) SEQUENCE CHARACTERISTICS:
        ( A ) LENGTH: 88 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:42:

```
AATTCATGGG TATCGGTAAA TTCCTGCACT CCGCTAAGAA ATTCGGTAAA GCTTTCGTAG         60

GTGAAATCAT GAACTCTTAA TAAGTGCA                                          88
```

( 2 ) INFORMATION FOR SEQ ID NO:43:

( i ) SEQUENCE CHARACTERISTICS:
        ( A ) LENGTH: 108 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:43:

```
AATTCATGGC CTGTTACTGC CGTATTCCGG CATGCATCGC AGGCGAGCGT CGCTATGGTA         60

CTTGTATTTA CCAGGGTCGT CTGTGGGCAT TCTGTTGCTA ATAACTTA                   108
```

( 2 ) INFORMATION FOR SEQ ID NO:44:

( i ) SEQUENCE CHARACTERISTICS:
        ( A ) LENGTH: 108 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:44:

```
AGCTTAAGTT ATTAGCAACA GAATGCCCAC AGACGACCCT GGTAAATACA AGTACCATAG        60
CGACGCTCGC CTGCGATGCA TGCCGGAATA CGGCAGTAAC AGGCCATG                    108
```

( 2 ) INFORMATION FOR SEQ ID NO:45:

( i ) SEQUENCE CHARACTERISTICS:
        ( A ) LENGTH: 108 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:45:

```
AATTCATGGC CTGTTACTGC CGTATTCCGG CATGCATCGC AGGCGAGCGT CGCTATGGTA        60
CTTGTATTTA CCAGGGTCGT CTGTGGGCAT TCTGTTGCTA ATAACTTA                   108
```

( 2 ) INFORMATION FOR SEQ ID NO:46:

( i ) SEQUENCE CHARACTERISTICS:
        ( A ) LENGTH: 74 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:46:

```
AATTCATGCA GGCCCGTGCC ACCTGCTACT GTCGCACTGG TCGTTGTGCA ACGCGTGAAA        60
GCCTGAGCGG CGTC                                                          74
```

( 2 ) INFORMATION FOR SEQ ID NO:47:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:47:

```
GACGCCGCTC AGGCTTTCAC GCGTTGCACA ACGACCAGTG CGACAGTAGC AGGTGGCACG        60
GGCCTGCATG                                                               70
```

( 2 ) INFORMATION FOR SEQ ID NO:48:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:48:

```
TGTGAAATCT CCGGTCGTCT GTATCGCCTG TGTTGCCGTT AATAACTTA                    49
```

( 2 ) INFORMATION FOR SEQ ID NO:49:

( i ) SEQUENCE CHARACTERISTICS:
        ( A ) LENGTH: 53 base pairs
        ( B ) TYPE: nucleic acid
        ( C ) STRANDEDNESS: single ( D ) TOPOLOGY: linear ( x i ) SEQUENCE DESCRIPTION: SEQ ID NO:49:

AGCTTAAGTT ATTAACGGCA ACACAGGCGA TACAGACGAC CGGAGATTTC ACA   53

( 2 ) INFORMATION FOR SEQ ID NO:50:

( i ) SEQUENCE CHARACTERISTICS:
        ( A ) LENGTH: 123 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:50:

AATTCATGCA GGCCCGTGCC ACCTGCTACT GTCGCACTGG TCGTTGTGCA ACGCGTGAAA   60

GCCTGAGCGG CGTCTGTGAA ATCTCCGGTC GTCTGTATCG CCTGTGTTGC CGTTAATAAC   120

TTA   123

( 2 ) INFORMATION FOR SEQ ID NO:51:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 22
        ( D ) OTHER INFORMATION: /note= "Xaa = Lys modified by
        NH-2."

( x i ) SEQUENCE DESCRIPTION: SEQ ID NO:51:

Gly Ile Gly Lys Phe Leu Lys Lys Ala Lys Lys Phe Gly Lys Ala Phe
1               5                   10                  15

Val Lys Ile Leu Lys Xaa
            20

( 2 ) INFORMATION FOR SEQ ID NO:52:

( i ) SEQUENCE CHARACTERISTICS:
        ( A ) LENGTH: 101 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:52:

CTTATTAGCG CGGGCCACCC TGAATAGCGA TTGCGATACG GACTTATCGC TAACGCTATG   60

AGTTTTCCAG TTTCTTAGCA GTTTAGACA GCCAGGACAT G   101

( 2 ) INFORMATION FOR SEQ ID NO:53:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:53:

GTTATTAAGC TATCTTGCCC GCTATTTTCG CGATCTTACC TGCTATCTTT GCAATTTAC   60

CAGGGATTTT CAT   73

( 2 ) INFORMATION FOR SEQ ID NO:54:

( i ) SEQUENCE CHARACTERISTICS:
   ( A ) LENGTH: 122 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:54:

CTTATTATTT AGCGATCTGA GTAGCCTGGC CAACAACTGC TACAGCCGGA CCAGCTTTGA 60

TGATACCGTC GCGGATGTTC TGACCTACTT TCTCGATTTT CTTGAACAGT TTCCATTTCA 120

TG 122

( 2 ) INFORMATION FOR SEQ ID NO:55:

( i ) SEQUENCE CHARACTERISTICS:
      ( A ) LENGTH: 77 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:55:

CTTATTATTT CTTAAGGATC TTTACGAAAG CTTTACCGAA TTTCTTAGCT TTTTCAGGA 60

ATTTACCGAT ACCCATG 77

( 2 ) INFORMATION FOR SEQ ID NO:56:

( i ) SEQUENCE CHARACTERISTICS:
      ( A ) LENGTH: 56 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:56:

GATCTTATTA CAGTTTTTC AGAAGCTTTT TGAGTTTTTT CAGCAGTTTC TTCATC 56

( 2 ) INFORMATION FOR SEQ ID NO:57:

( i ) SEQUENCE CHARACTERISTICS:
      ( A ) LENGTH: 80 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:57:

GTTATTAACC TTTCTTAAGG ATCTTTACGA AAGCTTTACC GAATTCTTA GCTTTTTTCA 60

GGAATTTACC GATACCCTAG 80

( 2 ) INFORMATION FOR SEQ ID NO:58:

( i ) SEQUENCE CHARACTERISTICS:
      ( A ) LENGTH: 71 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:58:

AGCTTAGTTA TTAACGGCAT TTACGATAAC AGAAGCCACG GTAGCAGACG CGGAAACACC 60

AGCGACGCAT G 71

( 2 ) INFORMATION FOR SEQ ID NO:59:

( i ) SEQUENCE CHARACTERISTICS:
      ( A ) LENGTH: 75 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:59:

AGCTTAAGTT ATTAACCACG GCATTTACGA TAACAGAAGC CACGGTAGCA GACGCGGAAA 60

CACCAGCGAC GCATG 75

( 2 ) INFORMATION FOR SEQ ID NO:60:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:60:

CTTATTAAGA GTTCATGATT TCACCTACGA AAGCTTTACC GAATTTCTTA GCGGAGTCGA 60

GGAATTTACC GATACCCATG 80

( 2 ) INFORMATION FOR SEQ ID NO:61:

( i ) SEQUENCE CHARACTERISTICS:
        ( A ) LENGTH: 109 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:61:

AGCTTTAAGT TATTAGCAAC AGAATGCCCA CAGACGACCC TGGTAAATAC AAGTACCATA 60

GCGACGCTCG CCTGCGATGC ATGCCGGAAT ACGGCAGTAA CAGGCCATG 109

( 2 ) INFORMATION FOR SEQ ID NO:62:

( i ) SEQUENCE CHARACTERISTICS:
        ( A ) LENGTH: 123 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:62:

AGCTTAAGTT ATTAACGGCA ACACAGGCGA TACAGACGAC CGGAGATTTC ACAGACGCCG 60

CTCAGGCTTT CACGCGTTGC ACAACGACCA GTGCGACAGT AGCAGGTGGC ACGGGCCTGC 120

ATG 123

RECOMBINANT PRODUCTION OF BIOLOGICALLY ACTIVE PEPTIDES AND PROTEINS

BACKGROUND OF THE INVENTION

A. Field of the Invention

This invention relates to the production of biologically active amphiphilic peptides by recombinant techniques in bacterial host cells in which the peptide is expressed in high yield and is easily recovered. Despite the antimicrobial properties of the amphiphilic peptides, the claimed method avoids proteolytic degradation of the peptides and toxic effects on the host bacterial cells by expressing the peptides as fusion proteins in protease-deficient *E. coli* cells.

B. Description of the Prior Art

The development of recombinant DNA techniques and their application to the genetic engineering of microorganisms has dramatically changed our understanding of molecular and cellular biology during the past 20 years. These same techniques have also found useful applications in the production of rare or expensive biological molecules such as peptides and proteins of therapeutic value. Heterologous gene expression of therapeutic peptides and proteins has often been successful in organisms as diverse as bacteria, yeast, mammalian cells and, more recently, transgenic plants and animals.

The first choice for expressing therapeutic peptides and proteins has normally been the gram negative bacterium *Escherichia coli*. See, for example, *Methods in Enzymology*, Vol. 195 (D. Goeddel, ed.; Academic Press, New York, N.Y.; 1990); the description of the successful large scale production of recombinant human glucagon in *E. coli* by K. Yoshikawa et al. in *Journal of Protein Chemistry* 11, 517–525 (1992); and the expression of a recombinant salmon calcitonin precursor in *E. coli* by M. V. L. Ray et al. in *Bio/Technology* 11, 64–70 (1993).

There are, however, potential limitations in heterologous gene expression in *E. coli*, including toxicity of the foreign peptide or protein to the host cell, poor codon usage in the heterologous gene relative to the codon usage bias of the host cells, improper folding of recombinant gene products, and failed or inappropriate post-translational modification (e.g., glycosylation) of foreign proteins. These genetic engineering barriers have been studied and overcome to some degree. See, for example, D. V. Goeddel in *Methods in Enzymology*, Vol. 185 (D. V. Goeddel, ed., Academic Press, San Diego, Calif.; 1990), pp. 3–7 and A. L. Goldberg and S. A. Goff in *Maximizing Gene Expression* (W. Reznikoff and L. Gold, eds., Butterworth Publishers, Boston, Mass.; 1986), pp. 287–314.

Nonetheless, difficulties remain, particularly when expressing toxic peptides in *E. coli*. See, for example, the work of J. Lama and L. Carrasco on expression of toxic poliovirus polypeptides in *E. coli* in *Journal of Biological Chemistry* 267, 15932–15937 (1992) and *Biochem. Biophys. Research Comm.* 188, 972–981 (1992). These researchers found that expression of certain poliovirus proteins such as 3AB can be particularly toxic to *E. coli* hosts even when expressed in a highly regulated gene expression system such as the pET vectors developed by F. W. Studier and coworkers (cf. F. W. Studier et al., in *Methods in Enzymology*, Vol. 185 (D. V. Goeddel, ed., Academic Press, San Diego Calif. 1990), pp. 60–88).

Another limitation in heterologous gene expression in *E. coli* is the degradation of the proteins expressed. Many small peptides such as hormones and certain toxins are more susceptible to proteolytic degradation than large proteins. The proteolytic degradation of such peptides may be due to their relatively small size or to their lack of a highly ordered tertiary structure that would resist proteolytic degradation. See, for example, S. Gottesman in *Methods in Enzymology*, Vol. 185 (D. V. Goeddel, ed., Academic Press, San Diego, Calif.; 1990), pp. 119–129 and A. L. Goldberg and S. A. Goff in *Maximizing Gene Expression* (W. Reznikoff and L. Gold, eds., Butterworth, 1986), pp. 287–314.

Proteolytic degradation of expressed peptides may be reduced by producing peptides in the cytoplasm of bacteria as "inclusion bodies." Inclusion bodies are electron dense particles that consist of the recombinant protein and non-reducible polymers. See C. H. Schein, *Bio/Technology* 7, 1141–49 (1989). Unfortunately, however, useful peptides or proteins must be released from the inclusion bodies, requiring the use of strong chaotropic reagents, such as 6M urea or 8M guanidinium HCl. Such peptides and proteins may also require correct refolding or disulfide bond formation. Thus, the production of soluble recombinant peptides or proteins is preferred for the recombinant production of large quantities of therapeutically useful peptides or proteins, leaving unresolved the problem of proteolytic degradation of soluble peptides or proteins.

Another successful approach to reducing proteolytic degradation of expressed recombinant proteins or peptides is the use of protease-deficient host cell strains. It is widely understood in genetic engineering that protease-deficient host cell strains can increase yields of recombinant proteins, but there are no general means by which to predict what protease-deficient host cell strains are preferred in given instances. See, e.g., E. Bibi et al., *Proc. Natl. Acad. Sci. (U.S.A.)* 90, 9209–9213 (1993) on the utility of using *E. coli* ompT⁻ host strains for expressing a recombinant multidrug resistance (mouse mdr1) gene, and D. M. Alexander et al., *Protein Exp. and Purif.* 3 204–211 (1992) on the utility of *E. coli* lon⁻ host strains for expressing recombinant fibroblast growth factor. Bibi et al. found that ompT⁻ hosts allowed stable expression of multidrug resistance genes in *E. coli* whereas two lon⁻ host cell strains did not. By contrast, D. M. Alexander et al. obtained satisfactory expression of fibroblast growth factor in a lon⁻ host cell strain. In both of these references, the site of recombinant protein appearance (*E. coli* outer membrane for the mouse mdr1 gene product and cytoplasm for fibroblast growth factor) is associated with the preferred protease deficiency. That is, the ompT protease, also known as protease VII, is found in the outer membrane and lon is the major cytoplasmic ATP-dependent protease of *E. coli*. See K. R. Rupprecht et al., *J. Bacteriology* 153, 1104–1106 (1983); G. Gordon et al., *Mol. Gen. Genet.* 193, 414–421 (1984); and A. L. Goldberg and S. A. Goff in *Maximizing Gene Expression*, loc. cit.

A further alternative successful approach to stabilizing foreign peptide gene products which are inherently unstable or toxic is to express them fused to a host cell protein or to a virally-encoded protein which displays stability in the relevant host cell. There is an extensive literature on protein fusions, especially in the gene expression host *E. coli*. See, e.g., *Methods in Enzymology*, Vol. 185 (op. cit.). Commonly used *E. coli* fusion protein partners include *E. coli* maltose binding protein (malE), anthranilate synthetase (trpE), β-galactosidase (lacZ) and ribulokinase (araB), as well as Staph. aureus protein A, glutathione S-transferase of *Schistosoma japonicum* and the bacteriophage products of the cI gene of bacteriophage lambda and gene 10 of bacteriophage T7. See, for example, D. B. Smith et al., *Proc. Natl. Acad. Sci.*

(U.S.A.) 83, 8703–8707 (1986); J. H. Nunberg, U.S. Pat. No. 4,701,416 (issued Oct. 20, 1987); C. di Guan et al., *Gene* 67, 21–30 (1988); J. C. Edman et al., U.S. Pat. No. 4,820,642 (issued Apr. 11, 1989); F. W. Studier et al. in *Methods in Enzymology*, Vol. 185 (op. cit.), pp. 60–88; and F. W. Studier et al., U.S. Pat. No. 4,952,496 (issued Aug. 28, 1990).

Even fusions with the, for example, male maltose binding protein, however, are not always stable. For example, despite fusing CD4 (the HIV receptor protein on human lymphocytes) to the periplasmic form of maltose binding protein (MBP) of *E. coli*, the N-terminal 177 amino acids of CD4 underwent significant degradation when expressed in *E. coli*. See Szmelcman et al., *J. Acquired Immune Deficiency Syndromes* 3, 859–872 (1990).

Despite the observation of instability in some recombinant fusion proteins, several groups have used recombinant processes to express potentially toxic antimicrobial peptides as fusion proteins. For example, J. Lai et al. in World Patent Application WO 86/04356 (published Jul. 31, 1986) and U.S. Pat. No. 5,028,530 disclose the recombinant synthesis of free acid forms of natural and mutant amphiphilic and antimicrobial cecropin peptides, isolated from the moth *Hyalophora cecropia*, as fusion proteins with the *E. coli* araB gene product in *E. coli*. These proteins were expressed as inclusion bodies. As set forth above, a significant disadvantage of inclusion bodies is the requirement for chaotropic agents to release the protein.

K. L. Piers et al., *Gene* 134, 7–13 (1993) disclose the use of *E. coli* recombinant expression systems to produce fusion proteins containing antimicrobial peptides and enumerate the advantages of such systems. However, the fusion proteins isolated by K. L. Piers et al. were expressed either as inclusion bodies in *E. coli* or as secreted proteins in *Staph. aureus*. As set forth above, a significant disadvantage of inclusion body formation in the teaching of J. Lai et al. or K. L. Piers et al. is the requirement for chaotropic agents to release the fusion protein. Further, *Staph. aureus* is not an acceptable host cell for producing recombinant therapeutic proteins because of its role as a significant human pathogen.

J. Lai et al. (loc. cit.) and K. L. Piers et al. (loc. cit.) do not disclose any benefit of producing cecropin or other antimicrobial peptide fusion proteins in soluble form, nor do they suggest any beneficial effects of expressing mutant or derivative forms of the natural cecropins or other antimicrobial peptides since, e.g., in the case of J. Lai et al., their mutant cecropin A peptides displayed the same antimicrobial profile as the natural cecropin A (see Table IV of WO 86/04356). These researchers also claim their fusion proteins are not bacteriocidal, do not disclose any potential benefits of using protease-deficient host cells, and offer no solutions to efficient recombinant production of fusion proteins which display bacteriocidal properties, especially soluble fusion proteins.

M. Hellers et al., *Eur. J. Biochem* 199, 435–439 (1991), report the expression and secretion of the natural amphiphilic and antimicrobial peptide cecropin A at high levels in recombinant baculovirus cultured on *H. cecropia* pupal cells. The secreted product was correctly processed and was amidated to a significant extent, but they experienced difficulty in expressing cecropin B in the same system. Moreover, this recombinant gene expression is poorly suited for large scale production of therapeutic peptides or proteins.

J. Jaynes et al. disclose in WO 88/00976 and WO 89/04371 the utility of expressing natural and derivative cecropin peptide sequences as well as other amphiphilic and antimicrobial peptides in transgenic plants such as tobacco and rice, but they do not disclose enabling technology for expressing amphiphilic and antimicrobial peptides in microbial cell hosts nor the utility of such microbial expression. Similar technology relating to expression of antimicrobial magainin peptides in plants is revealed in EP Application No. 0 472 987 by N. F. Bascomb et al. and in EP Application No. 0 552 559 by B. Scheffler and M. Bevan, but again neither enabling technology nor benefits of expression of magainin peptides in microbial hosts is disclosed.

K. L. Piers et al. (loc. cit.) disclose production of two antimicrobial peptides, human defensin NP-1 and a synthetic cecropin-melittin hybrid peptide designated CEME, as fusion proteins in *E. coli*, but noted significant instability of their fusion proteins unless they inserted additional DNA sequences encoding a defensin pre-pro sequence between the fusion protein and the antimicrobial peptide. They made use exclusively of the *E. coli* host strain DH5α, which is protease proficient, and make no mention of any advantages conferred in using a protease-deficient *E. coli* host strain for expression of fusion proteins containing antimicrobial peptides. They also failed to obtain biologically active human defensin NP-1, which they ascribe to the inability of this defensin, which contains six cysteine residues, to form a proper disulfide array in their expression system. Thus, they did not identify any class of antimicrobial peptides with disulfide bridges which could be recovered in bioactive form in their expression systems without further biochemical processing or protein folding technology known in the art.

Thus, there is a need in the art for a process for the production of amphiphilic peptides by recombinant techniques in microbial hosts in which the peptide is expressed in high yield, may contain intramolecular disulfide bonds in the bioactive peptides, is not substantially degraded and is easily recovered, and the host cell is not otherwise negatively influenced to severely limit large scale production of such amphiphilic peptides.

There is also a need in the art for a process for the production of amphiphilic peptides which are modified post-translationally to improve their biological activity. It is known that amphiphilic peptides which are antimicrobial and/or inhibit the growth or proliferation of microbial pathogens have improved biological activity following amidation of their carboxyl terminus. See, e.g., J. H. Cuervo et al., *Peptide Res.* 1, 81–86 (1988) and J. Y. Lee et al., *Proc. Natl. Acad. Sci.* (USA) 86, 9159–9162 (1989). Enzymes such as peptidyl-glycine α-amidating monooxygenases are known which can amidate free carboxyl termini of peptides or proteins which terminate in a glycine residue, and such enzymes have been used to amidate the peptide hormone calcitonin, but the general utility of using amidating enzymes to post-translationally modify amphiphilic peptides is not known. Peptide substrate specificity in particular may be a strong limitation in modifying amphiphilic peptides. See P. P. Tamburini et al., *Int. J. Peptide Protein. Res.* 35, 153–156 (1990); Y. Iwasaki et al., *Eur. J. Biochem*, 201, 551–559 (1991); and M. V. L. Ray et al., *Bio/Technology* 11, 64–70 (1993). Similarly, chemical C-terminal amidation of unprotected peptides or proteins is generally difficult because of the potential for reaction of ε-amino groups on lysine or guanidino groups on arginine side chains with activated carboxyl terminal groups to form undesirable side products.

SUMMARY OF THE INVENTION

It is an object of the present invention to describe methods for producing and processing antimicrobial amphiphilic peptides which, despite the antimicrobial potency of such peptides, allow high levels of proteins to accumulate in certain protease-deficient microbial host cells and which also allow efficient recovery of full-length amphiphilic peptides.

In accordance with the invention, amphiphilic peptides are produced by a method comprising obtaining DNA encoding at least one amphiphilic peptide, inserting the DNA into an expression vector, transforming a protease-deficient microbial host with the expression vector, expressing the at least one amphiphilic peptide, and recovering and purifying the at least one amphiphilic peptide.

In another aspect, the amphiphilic peptides are produced by a method comprising obtaining DNA encoding at least one amphiphilic peptide, inserting the DNA into an expression vector containing the gene encoding at least a portion of a recombinant fusion protein partner, transforming a protease-deficient microbial host with the expression vector, expressing the recombinant fusion protein portion/amphiphilic peptide fusion protein, recovering and purifying the recombinant fusion protein portion/amphiphilic peptide fusion protein, and cleaving the fusion protein to obtain the at least one amphilic peptide.

In a preferred embodiment, the amphiphilic peptides are produced by a method comprising obtaining DNA encoding at least one amphiphilic peptide, inserting the DNA into an expression vector containing the gene encoding at least a portion of a carbohydrate binding protein, transforming an E. coli protease-deficient strain with the expression vector, expressing the carbohydrate binding protein portion/amphiphilic peptide fusion protein, recovering and purifying the carbohydrate binding protein portion/amphiphilic peptide fusion protein, and cleaving the fusion protein to obtain the at least one amphilic peptide. In a more preferred embodiment, the E. coli protease-deficient strain is a K-12 strain.

A simple extension of the method may also be applied to easily post-translationally amidate amphiphilic peptides produced by the method in high yield. The inventors have discovered that amphiphilic peptides produced by the method can be activated as C-terminal methyl esters and then converted with high efficiency to the amidated peptide form with external ammonia without requiring protection of lysine ε-amino or arginine guanidino side chain groups. Despite the potential of ε-amino side chain groups of lysine residues or guanidino groups of arginine residues for reacting with the peptide methyl ester to form various undesirable intramolecular and intermolecular reaction products, the inventors have found conversion of the methyl ester to the desired amide to proceed with an efficiency of at least 80% of the theoretical yield. The method has general utility for obtaining active antimicrobial peptides of diverse structure, including those with disulfide arrays.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE INVENTION

Figure 1:
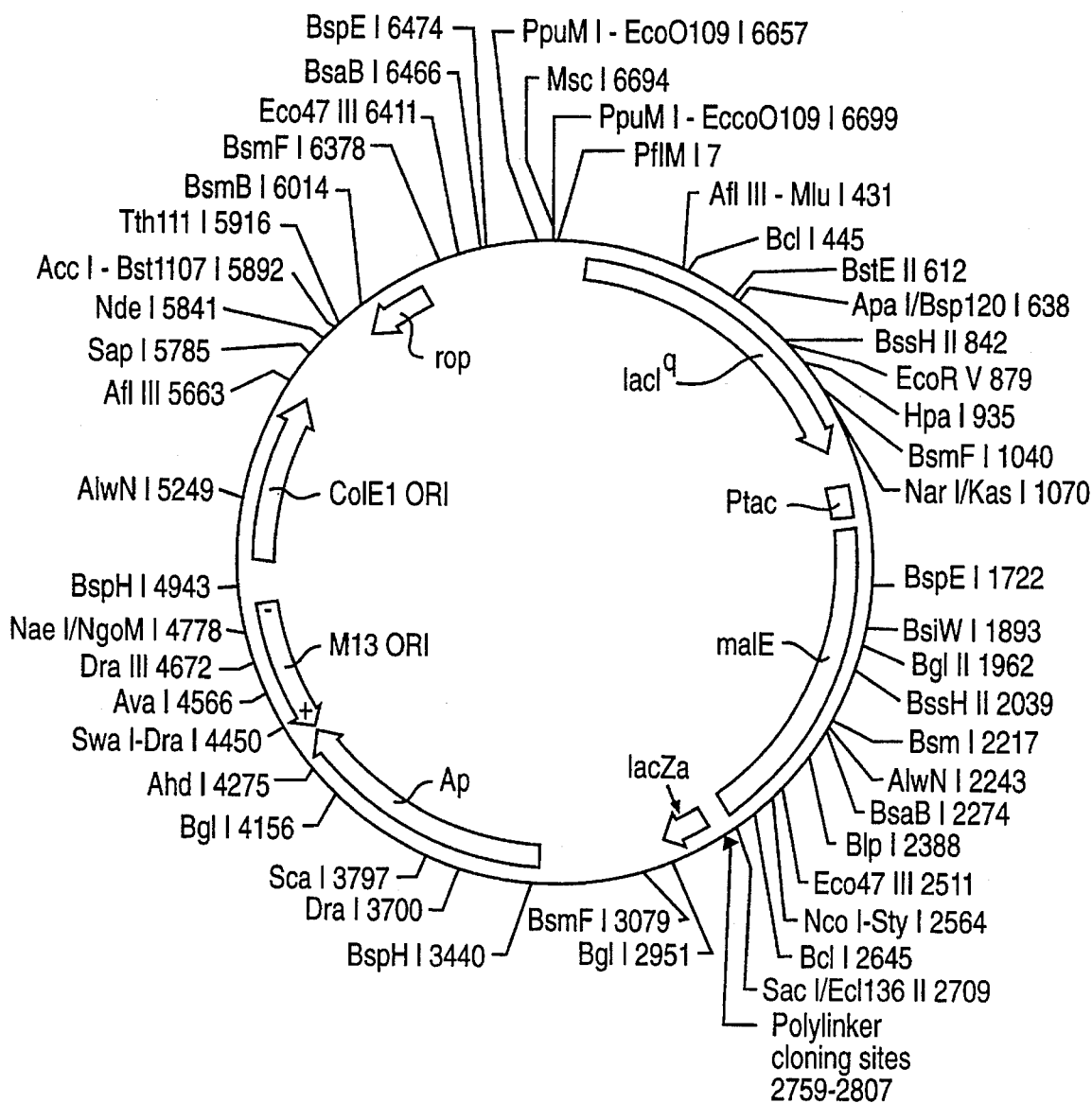
FIG. 1 is a restriction map of the pMAL™-c2 vector that can be used in the claimed method, showing the location of the malE gene and the site for the insertion of the DNA of the amphiphilic peptide of the invention.

The present invention relates to the recombinant production of amphiphilic peptides with biologically and therapeutically significant activities. In one embodiment, amphiphilic peptides are produced by a method comprising obtaining DNA encoding at least one amphiphilic peptide, inserting the DNA into an expression vector, transforming a protease-deficient microbial host with the expression vector, expressing the at least one amphiphilic peptide, and recovering and purifying the at least one amphiphilic peptide. In another aspect, the amphiphilic peptides are produced by a method comprising obtaining DNA encoding at least one amphiphilic peptide, inserting the DNA into an expression vector containing the gene encoding at least a portion of a recombinant fusion protein partner, transforming a protease-deficient microbial host with the expression vector, expressing the recombinant fusion protein portion/amphiphilic peptide fusion protein, recovering and purifying the recombinant fusion protein portion/amphiphilic peptide fusion protein, and cleaving the fusion protein to obtain the at least one amphiphilic peptide.

In a preferred embodiment, this invention relates to a method for producing amphiphilic peptides comprising obtaining DNA encoding the amphiphilic peptide, inserting the DNA into an expression vector containing a gene encoding at least a portion of a carbohydrate binding protein, transforming an E. coli protease-deficient host cell with the expression vector, expressing a carbohydrate binding protein portion/amphiphilic peptide fusion protein, recovering and purifying the carbohydrate binding protein portion/amphiphilic peptide fusion protein, and cleaving the fusion protein to obtain the amphiphilic peptide. In a preferred embodiment, the E. coli host cell is a K-12 strain.

In another preferred embodiment, the expression of the carbohydrate binding protein-amphiphilic peptide fusion proteins is under genetic regulation so as to limit expression of the fusion protein until an inducing stimulus is added to the E. coli culture.

In a more preferred embodiment, the carbohydrate binding protein of the present method is the entire male gene product of E. coli, also known as the maltose building protein. In a further more preferred embodiment, the carbohydrate binding protein of the present method is the first 121 amino acids of the male gene product of E. coli.

In still another preferred embodiment, purification of the fusion protein entails affinity chromatography of a protein solution containing fusion protein on a carbohydrate-containing matrix such as crosslinked amylose or amylose-agarose resin. Also in a preferred embodiment, cleavage to release the amphiphilic peptide is carried out using a chemical selected from a group comprising cyanogen bromide, hydroxylamine, or a mixture of hydroxylamine plus 2-nitro-5-thiocyano-benzoic acid.

In another aspect, this invention relates to the purification of amphiphilic compounds with biologically and therapeutically significant activities. More particularly, this invention relates to the purification of amphiphilic compounds, in particular amphiphilic peptides, which are able to inhibit, prevent, or destroy the growth or proliferation of target cells or viruses. Amphiphilic compounds in general are chemical entities which include both hydrophobic and hydrophilic moieties. Amphiphilic peptides are peptides or small proteins which have distinct regions or sequences of hydrophobic and hydrophilic amino acid residues. Amphiphilic peptides and proteins, because of their chemical character, may display both lipophilic (i.e., hydrophobic) and hydrophilic properties in non-aqueous and aqueous solvents, respectively, in some range of pH or an essentially equivalent acid-base chemical index.

In particular, many but not all amphiphilic peptides are capable of forming an alpha-helical structure, a stereospecific regular conformation of the peptide or protein chain defined by specific orientations of amino acid residue side chains in relationship to the main chain bonds; see T. E. Creighton, *Proteins, Structures and Molecular Principles* (W. H. Freeman and Co., New York, N.Y.; 1984). Conversely, many but not all alpha-helical peptides or small proteins are amphipathic; for example, poly-L-alanine can under certain conditions adopt an alpha-helical conformation which would not be an amphiphilic structure. The present invention specifically relates to amphiphilic peptides or small proteins which are capable of forming alpha-helical structures and lack cysteine residues or those which have cysteine residues but can adopt an amphiphilic conformation defined similarly to the convention used for defining alpha-helical amphiphilic peptides.

To determine if a peptide or small protein is amphiphilic within the context of the present invention, a geometric method may be used. See M. Schiffer and A. B. Edmundson, *Biophysical J.* 7, 121–135 (1967). The projection of the amino acid residues in an alpha-helical peptide or small protein on a plane perpendicular to the axis down the center of the helix yields an arrangement of the residues in a wheel pattern. A wheel pattern can be generated for any peptide or small protein by forcing the amino acid sequence in such peptides or proteins to conform to an alpha-helical structure. If the residues in the wheel pattern are classified as hydrophobic or hydrophilic by some commonly used biochemical index of such properties, then amphiphilic peptides are those which have a clear predominance of their hydrophilic residues on one side and most or all of their hydrophobic residues on the other side of some straight line through the center of the helical wheel projection and which bisects the wheel.

The amphiphilic character of other peptides or proteins which adopt some native conformation in a suitable solvent and which conformation is not an alpha helix also can be determined by a generalization of the above method. If some two-dimensional plane through the native conformation of a peptide or protein is defined so that a projection of the amino acid residues onto a plane perpendicular to the original plane yields a pattern through which some straight line can be drawn that intersects the original plane and approximately divides the pattern of residue projections into two equal portions, then the peptide or protein is amphiphilic if a clear predominance of hydrophobic residues falls on one side of the straight line and a clear predominance of hydrophilic residues falls on the other side of the straight line. A clear predominance of residues classified as either hydrophobic or hydrophilic is any proportion of the residues greater than 60% which would fall on one side or the other of the straight line defined geometrically above.

It is also possible to define an amphiphilic peptide or protein on the basis of the molecular hydrophobic moment of that peptide or protein in some suitable solvent. See D. Eisenberg et al., *Faraday Symp. Chem. Soc.* 17, 109–120 (1982).

The amphiphilic peptides of the present invention also, in general, are ion channel-forming peptides. As used herein, an ion channel-forming peptide or ionophore is a peptide which increases the permeability for ions across a natural or synthetic lipid membrane as determined by the method of B. Christensen et al., *Proc. Natl. Acad. Sci. (U.S.A.)* 85, 5072–5076 (1988).

The amphiphilic peptides of the claimed invention may be used as antimicrobial agents, antifungal agents, antiparasitic agents, antitumor agents, anticancer agents, and/or antiviral agents. As used herein, the term "antimicrobial peptide" will include but will not be limited to all these interpretive descriptions of the biological activity of amphiphilic peptides encompassed by the present invention.

Such peptides may be administered to a human or non-human animal or to plants to inhibit growth of a target cell or virus or virally-infected cell in the human or non-human animal or in the plant. Biologically active peptides encompassed by the present invention may also be employed to promote wound healing in a host. The peptides may increase collagen deposition at the site of a wound, enhance wound breaking strength, increase beneficial migration of cell types such as macrophages, neutrophils or epithelial cells, and/or reverse inhibition of wound healing in patients having compromised immune systems.

The potency and range of activity for an antimicrobial peptide can be determined by any of several techniques well known in microbiological practice. One such method is set forth in Example 1. In general, these techniques indicate the concentration of peptide necessary to completely inhibit the overnight growth of a bacterial inoculum or other microbial pathogen inoculum in suitable growth medium supplemented with various concentrations of peptide, or any other relevant endpoint such as minimum bactericidal concentration (M.B.C.), $M.I.C._{90}$, or surviving colony forming units (C.F.U.s).

Natural amphiphilic peptides which have antimicrobial, antitumor and/or wound healing properties have been previously reported and include but are not limited to peptides within the general classes termed abaecins, apidaecins, cecropins, CPF peptides, defensins, magainins, melittins, polyphemusins, tachyplesins, sarcotoxins, XPF peptides, and PGLa peptides. See, for example, D. Hultmark et al., U.S. Pat. No. 4,355,104 (granted Oct. 19, 1982); H. G. Boman and D. Hultmark, *Ann. Rev. Microbiol.* 41, 103–126 (1987); M. Zasloff, U.S. Pat. No. 4,810,777 (issued Mar. 7, 1989) (specifically incorporated herein by reference); B. A. Berkowitz et al., *Biochemical Pharmacology* 39, 625–629 (1990); T. Ganz et al., *European Journal of Haematology* 44, 1–8 (1990); R. Houghten et al., U.S. Pat. No. 4,962777 (issued Oct. 9, 1990); B. A. Berkowitz and L. Jacob, U.S. Pat. No. 5,045,531 (issued Sep. 3, 1991); H. G. Boman, *Cell* 65, 205–207 (1991); M. Zasloff, U.S. Pat. No. 5,073,542 (issued Dec. 17, 1992) (specifically incorporated herein by reference); and M. Zasloff, U.S. Pat. No. 5,202,420 (issued Apr. 13, 1993) (specifically incorporated herein by reference).

These peptides in general demonstrate only moderate or poor activity against at least one category of important human pathogenic agents such as pathogenic viruses, bacteria, fungi or parasites. For example, natural magainins such as Magainin I or Magainin II and insect cecropins such as cecropin A or cecropin B exhibit better antibacterial activity against many gram-negative bacterial pathogens, such as isolates of *E. coli, Bacteroides fragilis, Haemophilus influenzae* or *Pseudomonas aeruginosa*, than against gram positive bacteria, such as *Staphylococcus aureus* and *Streptococcus mutans*. See, for example, J. Lai et al., WO 86/04356, Table IV; H. Boman in U.S. Pat. No. 4,355,104 (issued Oct. 19, 1982); M. Zasloff in U.S. Pat. No. 4,810,777 (issued Mar. 7, 1989); and M. Zasloff in U.S. Pat. No. 5,073,542 (issued Dec. 17, 1992).

In contrast, natural defensins such as rabbit NP-1, human defensin HNP-1, or tracheal antimicrobial peptides exhibit better antibacterial activity against gram-positive bacteria than against gram-negative bacteria. See, for example, R. I. Lehrer et al., *Annu. Rev. Immunology* 11, 105–128 (1993); and M. Zasloff et al. in U.S. Pat. No. 5,202,420 (granted Apr. 13, 1993). A new class of antimicrobial peptides related to defensins recently has been isolated from bovine neutrophils by M. Selsted and coworkers and termed β-defensins. These natural antimicrobial peptides exhibit approximately equal activity against gram-negative and gram-positive bacteria but appear in general not to be quite as active as defensins (cf. M. E. Selsted et al., *Journal of Biol. Chem.* 268, 6641–6648 (1993)).

In addition to these natural peptides, the amphiphilic peptides of the present invention include modified analogs, such as those disclosed in the following commonly assigned applications: U.S. Ser. No. 07/908,455 to Maloy et al. for "Novel Peptide Compositions and Uses Therefor"; U.S. Ser. No. 08/133,740 to Maloy for "Compositions of and Treatment with Biologically Active Peptides Having D-Amino Acid Residues"; U.S. Ser. No. 07/713,716 to Maloy and Kari for "Composition and Treatment with Biologically Active Peptides Having C-terminal Substitutions"; U.S. Ser. No. 08/184,462 to Berkowitz and Jacob for "Biologically Active Peptides Having N-terminal Substitutions"; U.S. Ser. No. 08/199,553 to Kari for "Amino Acids and Peptides Having Modified C-terminals and N-terminals;" U.S. Ser. No. 07/944,370 to Maloy et al. for "Prophylaxis and Treatment of Adverse Oral Conditions with Biologically Active Peptides;" all of which are specifically incorporated herein by reference.

Unlike most of these natural and analogous peptides, the biologically active antimicrobial and amphiphilic peptides produced by the claimed method exhibit a broader range of activity and/or greater potency than related peptides of natural origin. In one embodiment, the amphiphilic peptides of the present invention include recombinantly produced versions of the natural peptides described above. In a preferred embodiment, the amphiphilic peptides of the present invention include but are not limited to:

| | |
|---|---|
| Cecropin P1: (SEQ ID NO: 1) | $NH_2$—SWLSKTAKKLENSAKKRISEGIAIAIQGGPR—OH |
| MSI-55: (free acid form of MSI-103) (SEQ ID NO: 2) | $NH_2$—KIAGKIAKIAGKIAKIAGKIA—OH |
| Cecropin A: (SEQ ID NO: 3) | $NH_2$—KWKLFKKIEKVGQNIRDGIIKAGPAVAVVGQATQIAKG |
| MSI-344: (SEQ ID NO: 4) | $NH_2$—GIGKFLKKAKKFGKAFVKILKK—OH |
| MSI-420, free acid form: (SEQ ID NO: 5) | $NH_2$—KKLLKKLKKLLKKL—OH |
| MSI-556: (SEQ ID NO: 6) | $NH_2$—GIGKFLKKAKKFGKAGVKILKKG—OH |
| Polyphemusin I, free acid form: (SEQ ID NO: 7) | $NH_2$—RRWCFRVCYRGFCYRKCR—OH |
| Lim1: (SEQ ID NO: 8) | $NH_2$—RRWCFRVCYRGFCYRKCRG—OH |
| Magainin 2 (SEQ ID NO: 9) | $NH_2$—GIGKFLHSAKKFGKAFVGEIMNS—OH |
| human NP-1: (SEQ ID NO: 10) | $NH_2$—ACYCRIPACIAGERRYGTCIYQGRLWAFCC—OH |
| putative human defensin 5: (SEQ ID NO: 11) | $NH_2$—QARATCYCRTGRCATRESLSGVCEISGRRYRLCCR—OH |

In a preferred embodiment, the DNA of preferred amphiphilic peptides is comprised of chemically synthesized oligonucleotides selected from the following:

Cecropin P1:

5'- CTT—ATT—AGC—GCG—GGC—CAC—
CCT—GAA—TAG—CGA—TTG—CGA—TAC—
CTT—CA-3'
(SEQ ID NO: 12)

+

5'- AAT—TCA—TGT—CCT—GGC—TGT—

Cecropin P1:

CTA—AAA—CTG—CTA—AGA—AAC—TGG—
AAA—ACT—CCG—CTA—AA-3'
(SEQ ID NO: 13)

+

5'- AAA—CGC—ATC—TCT—GAA—GGT—
ATC—GCA—ATC—GCT—ATT—CAG—GGT—
GGC—CCG—CGC—TAA—TAA—GTG—CA-3'
(SEQ ID NO: 14)

+

5'- GAG—ATG—CGT—TTT—TTA—GCG—
GAG—TTT—TCC—AGT—TTC—TTA—GCA—
GTT—TTA—GAC—AGC—CAG—GAC—ATG-3'
(SEQ ID NO: 15)

assembled by techniques known to those skilled in the art to produce

5'- AAT—TCA—TGT—CCT—GGC—TGT—CTA—AAA—
3'-GT—ACA—GGA—CCG—ACA—GAT—TTT—
CTG—CTA—AGA—AAC—TGG—AAA—ACT
GAC—GAT—TCT—TTG—ACC—TTT—TGA
CCG—CTA—AAA—AAC—GCA—TCT—CTG—AAG—
GTA—TCG—CAA—TCG—CTA—TTC—AGG
GGC—GAT—TTT—TTG—CGT—AGA—GAC—TTC—
CAT—AGC—GTT—AGC—GAT—AAG—TCC
GTG—GCC—CGC—GCT—AAT—AAG—TGC—A-3'
CAC—CGG—GCG—CGA—TTA—TTC-5'
(SEQ ID NO. 16 top strand;
SEQ ID NO. 52 bottom strand).

MSI-55:

5'- ATG—AAA—ATC—GCT—GGT—AAA—
ATT—GCA—AAG—ATA—GCA—GGT—AAG—
ATC—GCG—AAA—ATA—GCG—GGC—AAG—
ATA—GCT—TAA—TAA—CTG—CA-3'
(SEQ ID NO. 17)

+

5'- GTT—ATT—AAG—CTA—TCT—TGC—
CCG—CTA—TTT—TCG—CGA—TCT—TAC—
CTG—CTA—TCT—TTG—CAA—TTT—TAC—
CAG—CGA—TTT—TCA—T-3'
(SEQ ID NO: 18)

assembled by techniques known to those skilled in the art to produce

5'- ATG—AAA—ATC—GCT—GGT—AAA—
3'- TAC—TTT—TAG—CGA—CCA—TTT—
ATT—GCA—AAG—ATA—GCA—GGT—AAG—
TAA—CGT—TTC—TAT—CGT—CCA—TTC—
ATC—GCG—AAA—ATA—GCG—GGC—AAG—
TAG—CGC—TTT—TAT—CGC—CCG—TTC—
ATA—GCT—TAA—TAA—CTG—CA-3'
TAT—CGA—ATT—ATT—G-5'
(SEQ ID NO. 19 top strand:
SEQ ID NO. 53 bottom strand).

Cecropin A:

5'- AA—TTC—ATG—AAA—TGG—AAA—
CTG—TTC—AAG—AAA—ATC—GAG—AAA—
GTA—GGT—CAG—AAC—ATC—CGC-3'
(SEQ ID NO: 20)

+

5'- C—TTA—TTA—TTT—AGC—GAT—
CTG—AGT—AGC—CTG—GCC—AAC—AAC—
TGC—TAC—AGC—CGG—ACC—A-3'
(SEQ ID NO: 21)

+

5'- GAC—GGT—ATC—ATC—AAA—GCT—
GGT—CCG—GCT—GTA—GCA—GTT—GTT—

```
            GGC—CAG—GCT—ACT—CAG—ATC—GCT—
            AAA—TAA—TAA—GTG—CA-3'
            (SEQ ID NO: 22)
          +
        5'- GC—TTT—GAT—GAT—ACC—GTC—
            GCG—GAT—GTT—CTG—ACC—TAC—TTT—
            CTC—GAT—TTT—CTT—GAA—CAG—TTT—
            CCA—TTT—CAT—G-3'
            (SEQ ID NO: 23)
``` assembled by techniques known to those skilled in the art to produce

```
        5'- AAT—TCA—TGA—AAT—GGA—AAC—TGT—
        3'- GT—ACT—TTA—CCT—TTG—ACA—
            TCA—AGA—AAA—TCG—AGA—AAG—TAG—GTC
            AGT—TCT—TTT—AGC—TCT—TTC—ATC—CAG
            AGA—ACA—TCC—GCG—ACG—GTA—TCA—
            TCT—TGT—AGG—CGC—TGC—CAT—AGT—
            TCA—AAG—CTG—GTC—CGG—CTG—TAG—CAG
            AGT—TTC—GAC—CAG—GCC—GAC—ATC—GTC
            TTG—TTG—GCC—AGG—CTA—CTC—AGA—
            AAC—AAC—CGG—TCC—GAT—GAG—TCT—
            TCG—CTA—AAT—AAT—AAG—TGC—A-3'
            AGC—GAT—TTA—TTA—TTC-5'
            (SEQ ID NO. 24 top strand;
            SEQ ID NO. 54 bottom strand).
MSI-344:
        5'- AAT—TC—ATG—GGT—ATC—GGT—
            AAA—TTC—CTG—AAA—AAA—GCT—AAG—
            AAA—TTC—GGT—AAA—GCT—TTC—GTA—
            AAG—ATC—CTT—AAG—AAA—TAA—TAA—
            GTG—CA-3'
            (SEQ ID NO: 25)
          +
        5'- C—TTA—TTA—TTT—CTT—AAG—
            GAT—CTT—TAC—GAA—AGC—TTT—ACC—
            GAA—TTT—CTT—AGC—TTT—TTT—CAG—
            GAA—TTT—ACC—GAT—ACC—CAT—G-3'
            (SEQ ID NO: 26)
``` assembled by techniques known to those skilled in the art to produce

```
        5'- AAT—TC—ATG—GGT—ATC—GGT—
        3'-G—TAC—CCA—TAG—CCA—
            AAA—TTC—CTG—AAA—AAA—GCT—AAG—
            TTT—AAG—GAC—TTT—TTT—CGA—TTC—
            AAA—TTC—GGT—AAA—GCT—TTC—GTA—
            TTT—AAG—CCA—TTT—CGA—AAG—CAT—
            AAG—ATC—CTT—AAG—AAA—TAA—TAA—
            TTC—TAG—GAA—TTC—TTT—ATT—ATT—
            GTG—CA-3'
            C-5'
            (SEQ ID NO. 27 top strand;
            SEQ ID NO: 55 bottom strand).
MSI-420:
        5'- GAT—CGA—TGA—AGA—AAC—TGC—
            TGA—AAA—AAC—TCA—AAA—AGC—TTC—
            TGA—AAA—AAC—TGT—AAT—AA-3'
            (SEQ ID NO: 28)
          +
        5'- GAT—CTT—ATT—ACA—GTT—TTT—
            TCA—GAA—GCT—TTT—TGA—GTT—TTT—
            TCA—GCA—GTT—TCT—TCA—TC-3'
            (SEQ ID NO: 29)
``` assembled by techniques known to those skilled in the art to produce

```
5'-GAT—CGA—TGA—AGA—AAC—TGC—
   3'-CT—ACT—TCT—TTG—ACG—

TGA—AAA—AAC—TCA—AAA—AGC—TTC—
   ACT—TTT—TTG—AGT—TTT—TCG—AAG—

TGA—AAA—AAC—TGT—AAT—AA-3'
   ACT—TTT—TTG—ACA—TTA—TTC—TAG-5'
```

(SEQ ID NO. 30 top strand; SEQ ID NO. 56 bottom strand

MSI-556:
```
5'-AAT—TCA—TGG—GTA—TCG—GTA—AAT—TCC—TGA—AAA—AAG—CTA—

AGA—AAT—TCG—GTA—AAG—CTT—TCG—TAA—AGA—TCC—TTA—AGA—AAG—

GTT—AAT—AAC—TGC—A-3'
```

(SEQ ID NO: 31)

+

```
5'-GTT—ATT—AAC—CTT—TCT—TAA—GGA—TCT—TTA—CGA—AAG—CTT—

TAC—CGA—ATT—TCT—TAG—CTT—TTT—TCA—GGA—ATT—TAC—CGA—TAC—

CCA—TG-3'
```

(SEQ ID NO: 32)

assembled by techniques known to those skilled in the art to produce

```
5'-AAT—TCA—TGG—GTA—TCG—GTA—AAT—TCC—TGA—AAA—AAG—CTA—
   3'-GA—TCC—CAT—AGC—CAT—TTA—AGG—ACT—TTT—TTC—GAT—

AGA—AAT—TCG—GTA—AAG—CTT—TCG—TAA—AGA—TCC—TTA—AGA—AAG—
   TCT—TTA—AGC—CAT—TTC—GAA—AGC—ATT—TCT—AGG—AAT—TCT—TTC—

GTT—AAT—AAC—TGC—A-3'
   CAA—TTA—TTG-5'
```

(SEQ ID NO: 33 top strand; SEQ ID NO: 57 bottom strand)

Polyphemusin I:
```
5'-AAT—TCA—TGC—GTC—GCT—GGT—
   GTT—TCC—GCG—TCT—GCT—ACC—GTG—
   GCT—TCT—GTT—ATC—GTA—AAT—GCC—
   GTT—AAT—AAC—TAA-3'
```
(SEQ ID NO: 34)

+

```
5'-AGC—TTA—AGT—TAT—TAA—
   CGG—CAT—TTA—CGA—TAA—CAG—AAG—
   CCA—CGG—TAG—CAG—ACG—CGG—AAA—
   CAC—CAG—CGA—CGC—ATG-3'
```
(SEQ ID NO: 35)

assembled by techniques known to those skilled in the art to produce

```
5'-AAT—TCA—TGC—GTC—GCT—GGT—
   3'-GT—ACG—CAG—CGA—CCA—

GTT—TCC—GCG—TCT—GCT—ACC—GTG—
   CAA—AGG—CGC—AGA—CGA—TGG—CAC—

GCT—TCT—GTT—ATC—GTA—AAT—GCC—
   CGA—AGA—CAA—TAG—CAT—TTA—CGG—

GTT—AAT—AAC—TAA-3'
   CAA—TTA—TTG—ATT—CGA-5'
```

(SEQ ID NO: 36 top strand; SEQ ID NO: 58 bottom strand).

Lim1:
```
5'-AAT—TCA—TGC—GTC—GCT—GGT—
   GTT—TCC—GCG—TCT—GCT—ACC—GTG—
   GCT—TCT—GTT—ATC—GTA—AAT—GCC—
   GTG—GTT—AAT—AAC—TTA-3'
```
(SEQ ID NO: 37)

+

```
5'-AGC—TTA—AGT—TAT—TAA—CCA—
   CGG—CAT—TTA—CGA—TAA—CAG—AAG—
   CCA—CGG—TAG—CAG—ACG—CGG—AAA—
   CAC—CAG—CGA—CGC—ATG-3'
   (SEQ ID NO: 38)
``` assembled by techniques known to those skilled in the art to produce

```
5'-AAT—TCA—TGC—GTC—GCT—GGT—
   3'-GT—ACG—CAG—CGA—CCA—

GTT—TCC—GCG—TCT—GCT—ACC—GTG—
   CAA—AGG—CGC—AGA—CGA—TGG—CAC—

GCT—TCT—GTT—ATC—GTA—AAT—GCC—
   CGA—AGA—CAA—TAG—CAT—TTA—CGG—

GTG—GTT—AAT—AAC—TTA-3'
   CAC—CAA—TTA—TTG—AAT—TCG—A-5'

(SEQ ID NO. 39 top strand; SEQ ID NO. 59 bottom strand).
```

Magainin 2:
```
5'-AAT—TCA—TGG—GTA—TCG—GTA—
   AAT—TCC—TGC—ACT—CCG—CTA—AGA—
   AAT—TCG—GTA—AAG—CTT—TCG—TAG—
   GTG—AAA—TCA—TGA—ACT—CTT—AAT—
   AAG—TGC—A-3'
   (SEQ ID NO: 40)
```

+

```
5'-CTT—ATT—AAG—AGT—TCA—TGA—
   TTT—CAC—CTA—CGA—AAG—CTT—TAC—
   CGA—ATT—TCT—TAG—CGG—AGT—GCA—
   GGA—ATT—TAC—CGA—TAC—CCA—TG-3'
   (SEQ ID NO: 41)
``` assembled by techniques known to those skilled in the art to produce

```
5'-AAT—TCA—TGG—GTA—TCG—GTA—
   3'-GT—ACC—CAT—AGC—CAT—

AAT—TCC—TGC—ACT—CCG—CTA—AGA—
   TTA—AGG—AGC—TGA—GGC—GAT—TCT—

AAT—TCG—GTA—AAG—CTT—TCG—TAG—
   TTA—AGC—CAT—TTC—GAA—AGC—ATC—

GTG—AAA—TCA—TGA—ACT—CTT—AAT—
   CAC—TTT—AGT—ACT—TGA—GAA—TTA—

AAG—TGC—A-3'
   TTC-5'

(SEQ ID NO. 42 top strand; SEQ ID NO. 60 bottom strand).
```

HUMAN NP-1:
```
5'-AAT—TCA—TGG—CCT—GTT—ACT—GCC—GTA—TTC—CGG—
   CAT—GCA—TCG—CAG—GCG—AGC—GTC—GCT—ATG—
   GTA—CTT—GTA—TTT—ACC—AGG—GTC—GTC—TGT—
   GGG—CAT—TCT—GTT—GCT—AAT—AAC—TTA-3'
   (SEQ ID NO: 43)
```

+

```
5'-AGC—TTA—AGT—TAT—TAG—CAA—CAG—AAT—GCC—CAC—
   AGA—CGA—CCC—TGG—TAA—ATA—CAA—GTA—CCA—
   TAG—CGA—CGC—TCG—CCT—GCG—ATG—CAT—GCC—
   GGA—ATA—CGG—CAG—TAA—CAG—GCC—ATG-3'
   (SEQ ID NO: 44)
``` assembled by techniques known to those skilled in the art to produce

```
5'-AAT—TCA—TGG—CCT—GTT—ACT—GCC—GTA—TTC—CGG—
3'-GT —ACC—GGA—CAA—TGA—CGG—CAT—AAG—GCC—

CAT—GCA—TCG—CAG—GCG—AGC—GTC—GCT—ATG—
   GTA—CGT—AGC—GTC—CGC—TCG—CAG—CGA—TAC—

GTA—CTT—GTA—TTT—ACC—AGG—GTC—GTC—TGT—
   CAT—GAA—CAT—AAA—TGG—TCC—CAG—CAG—ACA—

GGG—CAT—TCT—GTT—GCT—AAT—AAC—TTA-3'
   CCC—GTA—AGA—CAA—CGA—TTA—TTG—AAT—TTC—GA-5'

(SEQ ID NO. 45 top strand; SEQ ID NO. 61 bottom strand)
```

Putative Human defensin 5:
```
5'-AAT—TCA—TGC—AGG—CCC—GTG—CCA—CCT—GCT—ACT—
   GTC—GCA—CTG—GTC—GTT—GTG—CAA—CGC—GTG—
   AAA—GCC—TGA—GCG—GCG—TC-3'
(SEQ ID NO: 46)
```

+

```
5'-GAC—GCC—GCT—CAG—GCT—TTC—ACG—CGT—TGC—ACA—
   ACG—ACC—AGT—GCG—ACA—GTA—GCA—GGT—GGC—
   ACG—GGC—CTG—CAT—G-3'
(SEQ ID NO: 47)
```

+

```
5'-TGT—GAA—ATC—TCC—GGT—CGT—CTG—TAT—CGC—CTG—
   TGT—TGC—CGT—TAA—TAA—CTT—A-3'
(SEQ ID NO: 48)
```

+

```
5'-AGC—TTA—AGT—TAT—TAA—CGG—CAA—CAC—AGG—CGA—
   TAC—AGA—CGA—CCG—GAG—ATT—TCA—CA-3'
(SEQ ID NO: 49)
``` assembled by techniques known to those skilled in the art to produce

```
5'-AAT—TCA—TGC—AGG—CCC—GTG—CCA—CCT—
3'-GT—ACG—TCC—GGG—CAC—GGT—GGA—

GCT—ACT—GTC—GCA—CTG—GTC—GTT
   CGA—TGA—CAG—CGT—GAC—CAG—CAA

GTG—CAA—CGC—GTG—AAA—GCC—TGA—
   CAC—GTT—GCG—CAC—TTT—CGG—ACT—

GCG—GCG—TCT—GTG—AAA—TCT—CCG—GTC
   CGC—CGC—AGA—CAC—TTT—AGA—GGC—CAG

GTC—TGT—ATC—GCC—TGT—GTT—GCC—GTT—
   CAG—ACA—TAG—CGG—ACA—CAA—CGG—CAA—

AAT—AAC—TTA-3'
   TTA—TTG—AAT—TCGA-5'
```

(SEQ ID NO. 50 top strand; SEQ ID NO. 62 bottom strand)

In the method of the claimed invention, the DNA encoding the amphiphilic peptides of the invention may be obtained by any of the many methods known to those of ordinary skill in this art. These methods include the synthesis of synthetic genes using oligonucleotides prepared by the phosphodiester approach or, more preferably, the phosphite-triester method as set forth in, e.g., M. H. Caruthers et al., "New Methods for Synthesizing Deoxyoligonucleotides", *Genetic Engineering* (J. K. Setlow and A. Hollaender, eds., Plenum Press New York and London; 1982), pp. 119–145, which is specifically incorporated by reference. The oligonucleotides of the invention may also be prepared with a commercially-available synthesizer such as the Applied Biosystems (Foster City, Calif.) model 392 oligonucleotide synthesizer.

Alternatively, the DNA of the amphiphilic peptide may be "cut" from a plasmid or other source of DNA by use of restriction endonucleases or restriction enzymes. Restriction enzymes are enzymes, isolated chiefly from prokaryotes, that recognize specific sequences within double-stranded DNA and cleave the sequence at known and specific sites. Those of ordinary skill in this art are familiar with the hundreds of restriction enzymes used to cleave DNA, such as XmnI, EcoRI, BamHI, XbaI, SalI, PstI, and HindIII. For a discussion of restriction enzymes, their characteristics, and uses, see T. Maniatis et al., *Molecular Cloning: A Laboratory Manual* (Cold Spring Harbor Laboratory 1982) and R. W. Old and S. B. Primrose, *Principles of Gene Manipulation* (Blackwell Scientific Publ. 3rd ed. 1985), both of which are specifically incorporated herein by reference.

The DNA obtained by either method is then inserted into an expression vector that contains the gene encoding some portion of a carbohydrate binding protein. As used herein, an "expression vector" refers to a plasmid or phage DNA or other DNA sequence which contains one or more endonuclease recognition sites at which the DNA sequence may be cut for the insertion of foreign DNA and which is capable of replicating in a host cell and expressing the foreign gene in a host cell, generally under the control of regulatory sequences. The expression vector is also termed an expression vehicle.

The selection of the expression vector is within the routine skill of those in this art. Exemplary expression vectors include but are not limited to Bluescript, pBR322, pET3a-d, pET11a-d, pEX 1–3, pEZZ 18, pGEX, pKK233-2, pMAL, pMC1871, pRIT2T, pSE280 and pSE380, pTrcHis, and pUC18/19.

In a preferred embodiment, the expression vector has a deleted or inactivated rop function. The rop gene encodes a small protein (63 amino acids) which limits plasmid copy number. Removal or mutation of this trans-complementable locus leads to increased plasmid copy number and potentially to increased expression levels of recombinant proteins. See A. J. Twigg and D. Sheratt, *Nature* 283, 216–218 (1980); M. Muesing et al., *Cell* 24, 235–242 (1981); and M. W. Zoronfleh and T. Ho, *Biotechnology Letters* 15, 337–340 (1993). The inventors have discovered that rop expression vectors of the present invention derived by deletion of the rop locus exhibit increased plasmid copy number and increased levels of expression when compared to fusion proteins from homologous rop$^+$ expression vectors. In a more preferred embodiment, the top locus is deleted from colE1 replicons which are parent expression vectors for carbohydrate binding protein portion/amphiphilic peptide fusion proteins. In a most preferred embodiment, the rop locus is deleted from expression vectors derived from the plasmid pBR322 between the unique MscI and Bst 1107I restriction enzyme recognition sites.

The expression vector of the claimed method preferably contains a gene encoding some portion of a fusion protein partner. The preferred fusion protein partner is a carbohydrate binding protein ("CBP"). Such proteins are advantageous in that they may permit a one-step purification based on the affinity of the protein for a carbohydrate. Such proteins or portions of a protein are also advantageous in that they may exhibit long half lives in a suitable host cell, thereby providing greater yields of fusion protein.

In a preferred embodiment, the carbohydrate binding protein is a maltose binding protein ("MBP") that has an affinity for maltose, amylose, and other related sugars. In a more preferred embodiment, the MBP is the product of the *E. coli* male gene. In another preferred embodiment, the MBP is the first 121 N-terminal amino acids of the *E. coli* malE gene product. In one embodiment, the malE gene of *E. coli* is available in plasmids known as the pMAL™ vectors (FIG. 1) from New England Biolabs, Beverly Mass.

In another embodiment, the CBP is all or some portion of the B-chain of the protein ricin toxin isolated from the seeds of the castor oil plant *Ricinus communis*. In a more specific embodiment, the CBP is at least the 120 N-terminal amino acids of the B-chain of the protein ricin toxin. For a general discussion of such a CBP, see Richardson, P. T. et al. *Biochemica et Biophysica Acta.* 950, 385–394 (1988); Hussain, K. et al., *FEB* 244(2), 383–387 (Feb. 1984); Wales R., *J. Biological Chemistry* 266 (29), 19172–79 (1991); and Rutenberg, E., PROTEINS: *Structure, Function, and Genetics*, 10, 260–269 (1991).

The insertion of the DNA of the amphiphilic peptides into the expression vector is routine for those skilled in this art. In one embodiment, restriction enzymes are first used to cut the expression vector open at specific known and desired sites. The foreign DNA is introduced and joined to the expression vector. Any of the methods commonly used for the joining may be used, including, for example, the use of T4 DNA ligase to covalently join the annealed cohesive ends produced by certain restriction enzymes, the use of DNA ligase from phage T4-infected *E. coli* to catalyze the formation of phosphodiester bonds between blunt-ended fragments, and the use of terminal deoxynucleotidyl-transferase to synthesize complementary homopolymeric 3'-single stranded tails at the ends of the fragments which can be annealed and then repaired in vivo. For a general discussion of such methods, see R. W. Old and S. B. Primrose, *Principles of Gene Manipulation* (Blackwell Scientific Publ. 3rd ed. 1985).

In the preferred embodiment using the pMAL™ vectors, the DNA of the amphiphilic peptide is inserted into the polylinker region between the malE gene and lacZα, a gene segment that is downstream from the malE gene, using unique restriction sites between malE and lacZα.

The resulting expression vector is then used to transform a host cell. The invention is directed to the use of any protease-deficient microbial host cell, such as yeast strains deficient in one or more of the proteases encoded by the genes PrA, PrB, CpY, CpS, ApI, or ApCo; *Bacillus subtilis* strains deficient in one or more of the proteases encoded by the genes Apr (subtilisin), Npr, Isp-1, or Epr; or *E. coli* strains deficient in one or more of the proteases encoded by the genes Lon, OmpT, ClpA, DegP, or HtpR.

The host cell that is the preferred subject of the claimed invention is a protease-deficient *E. coli*. As set forth in the Background, *E. coli* is the host cell of first choice for the expression of peptides and proteins. Nonetheless, not all strains of *E. coli* are acceptable, particularly where the host is to be used for the expression of therapeutic peptides or proteins. For example, the strain or its parent should be listed on the United States Food and Drug Administration "Generally Rated As Safe" (GRAS) list. One such *E. coli* strain that is listed on the GRAS list is K-12. K-12 is advantageous because it has low levels of pyrogen (such as endotoxin) and cannot colonize the human gut, and thus is a preferred host cell, but not even all K-12 strains are suitable for expressing therapeutic peptides.

Acceptable host cells also must have well defined genetics and a well-known cell lineage to avoid the use of cells with a mixed genome. A host with a mixed genome could introduce toxicities to the final product. For example, the strain HB101 has genetic material from *E. coli* B strains and has in the past likely been crossed with a pathogenic *Salmonella* strain.

Although those skilled in this art may be aware of a variety of proteases in which the host cells may be deficient, such as those described above, the preferred protease-deficient *E. coli* K-12 strains of the claimed invention are those strains deficient in lon, the major ATP-dependent protease of *E. coli*, and ompT, a major outer membrane-bound protease. See A. L. Goldberg and S. A. Goff in *Maximizing Gene Expression* (W. Reznikoff and L. Gold, eds.), Butterworth, Boston, Mass., 1986; pp. 287–314 and J. Grodberg and J. J. Dunn, *Journal of Bacteriology*, 170, 1245–1253 (1988). In more preferred embodiments of the present invention, the preferred protease-deficient *E. coli* K-12 strain is deficient in ompT.

The inventors have discovered by analysis of peptide formation in protease-deficient *E. coli* host strains that formation of a carbohydrate binding protein portion/amphiphilic peptide fusion protein as a cytoplasmic product in *E. coli* is subject to the proteolytic activities of both the lon protease and the ompT protease. Deletion or inactivation of either of these protease activities in a preferred *E. coli* host of the present method is sufficient to stabilize the fusion protein for maximal production of full length fusion protein. The inventors have also discovered that the amphiphilic peptide portion of a carbohydrate binding protein portion/amphiphilic peptide fusion protein is particularly sensitive to the direct or indirect action of either the lon and ompT proteases. The known substrate specificities of the proteases suggests the ompT protease is likely to be the more important protease in degrading amphiphilic peptides of the present invention. The inventors speculate that the ompT protease may act on a carbohydrate binding protein portion/amphiphilic peptide fusion protein during disruption of the host cell and harvesting of the cytoplasmic fusion protein. The inventors also speculate that the lon protease may act indirectly on the stability of the amphiphilic peptide portion of a carbohydrate binding protein portion/amphiphilic peptide fusion protein by controlling the abundance of the mature ompT protease through regulation of the processing of the ompT protease precursor. See R. C. Gayda et al., *Molec. Gen. Genet.* 175, 325–332 (1979), especially FIG. 3a–f.

In a preferred embodiment, the protease-deficient *E. coli* K-12 strains are selected from the group of strains comprising lon deletion strains including PR745 (New England Biolabs, Beverly, Mass.) and certain spontaneous fepA mutants of *E. coli* including UT400 and UT5600 (ompT⁻ derivatives of a W945 parent created from a chi1148 Roy Curtis strain as described by McIntosh et al., *J. Bacteriol.* 137, 653–657 (1979) and Elish et al. *J. Gen. Microbiol.* 134, 1355–1364 (1988)). In a more preferred embodiment, the protease-deficient *E. coli* K-12 strain is UT400. In addition to their recitations in the scientific literature, these strains are available from the *E. coli* Genetic Stock Center, Department of Biology, Yale University, New Haven, Conn. or from New England Biolabs, Beverly, Mass.

The host cells of the invention are then transformed with the expression vector containing the DNA of the amphiphilic peptide together with a gene encoding some portion of a carbohydrate binding protein. As used herein, transformation refers to the creation of a permanent genetic change induced in a host cell following incorporation of new DNA. Those of ordinary skill in the art are familiar with the techniques used for transformation, such as electroporation, transformation with calcium chloride or transformation with calcium chloride/rubidium chloride, as well as with the methods for optimizing the transforming conditions. For a general description of the methods used for transformation, see T. Maniatis et al., *Molecular Cloning: A Laboratory Manual* (Cold Spring Harbor Laboratory 1989), D. Hanahan in *J. Mol. Biol.* 166, 557–580 (1983), and *Current Protocols in Molecular Biology* (F. M. Ausubel et al., eds.), John Wiley and Sons, Media, Pa., revised 1993, Chapter 1.

The claimed method does not require the use of any specific transformation technique, but in a preferred embodiment the electroporation technique is used to transform the preferred protease-deficient host cells of the claimed invention.

Once transformed, the host cells are then introduced into a shake flask or bioreactor for replication and growth. The cell growth rate and yield are affected by physical and chemical environmental conditions, including temperature, pH, the availability of growth-limiting substrates, and the production of toxic metabolites. Product formation may be influenced by medium constituents (precursors, inducers, repressors, inhibitors), growth rate, morphology, oxygen/carbon dioxide concentration, temperature, pH, rate of substrate assimilation, and by-product secretion, among others. Additional factors that may be significant for use of a recombinant organism are foreign gene stability, high promoter control, high product expression, efficient product secretion, efficient glycosylation (if required), capacity for rapid growth, high product yield and productivity, high raw material utilization, minimization of recombinant product proteolysis and lack of endotoxin production. For a discussion of these issues, see O. P. Ward, *Bioprocessing* (Van Nostrand Reinhold, New York, 1991) pp. 1–14 and 121–136.

The optimization of such factors is well within the skill of those in this art and will vary according to host cell, expression vector, and recombinant product used and, accordingly, cannot limit the claimed invention. Applicants have, however, optimized certain factors for certain preferred host cells. For example, the UT400 cell line can be grown in LB broth (obtainable from GIBCO/BRL), LB broth+0.2% glucose, superbroth (constituents obtainable from GIBCO/BRL), and M9 minimal media+0.2% glucose+ yeast extract (HCD) media (constituents obtainable from GIBCO/BRL). These media may be prepared as follows:

LB medium per liter of final media
To 950 ml of deionized water, add:

| | |
|---|---|
| Bactotryptone | 10 g |
| Bacto-yeast extract | 5 g |
| NaCl | 10 g |

Stir to dissolve solutes. Adjust pH to 7.0 with 5N NaOH (~0.2 ml). Adjust volume to 1 liter with deionized water. Sterilize by autoclaving.

M9 Minimal Medium per liter of final media
To 750 ml of sterile deionized water, add:

| | |
|---|---|
| 5X M9 salts | 200 ml |
| 5X M9 = Na₂HPO₄7H₂O | 64 g/L |
| KH₂PO₄ | 15 g/L |
| NaCl | 2.5 g/L |
| NH₄Cl | 5.0 g/L |
| 20% solution of the appropriate carbon source | 20 ml |

If necessary, supplement with stock solutions of amino acids. Adjust final volume to 1 liter with deionized water. Adjust pH to 7.0 with 5N NaOH. Sterilize by autoclaving.

HCD Medium

| | |
|---|---|
| KH₂PO₄ | 13.3 g/L |
| (NH₄)₂HPO₄ | 4.0 g/L |
| Citric acid | 1.7 g/L |
| MgSO₄ + 2H₂O | 1.2 g/L |
| Trace Metals | 10.0 ml/L |
| Thiamine HCl | 4.5 mg/L (filter sterilize) |
| Glucose + H₂O | 27.5 g/L (25.0 g/L anhyd.) |

Autoclave KH₂PO₄, (NH₄)₂HPO₄, and citric acid in solution together. Autoclave MgSO₄, trace metals (recipe follows), and glucose separately. Filter sterilize thiamine HCl.

Trace Metals

| | |
|---|---|
| Ferric Citrate | 6.0 g/L |
| MnCl₂ + 4H₂O | 1.5 g/L |
| Zn(CH₃COO)₂ + 2H₂O | 0.8 g/L |
| H₃BO₃ | 0.3 g/L |
| Na₂MoO₄ + 2H₂O | 0.25 g/L |
| CoCl₂ + 6H₂O | 0.25 g/L |
| CaCl₂ + 2H₂O | 0.15 g/L |
| EDTA + 2H₂O | 0.84 g/L |

Glucose/Yeast Extract Feed
Autoclave yeast extract 80 g/L and glucose 200 g/L separately. Mix equal amounts for feed solution (40 g/L YE + 10% glucose).

Superbroth per liter of final media

| | |
|---|---|
| Tryptone | 35 grams |
| Yeast Extract | 20 grams |
| Sodium Chloride | 5 grams |

Another factor relevant to the growth of the transformed host cells is cell density. Although a range of cell densities is acceptable, it is within the skill of those in the art to optimize cell density. For example, in one embodiment of the invention, i.e., the growth of UT400 cells on superbroth plus glucose and yeast, it is possible to obtain a cell density of $1–2\times10^{11}$ CFU ($\approx$20 g/L dry cell weight, $OD_{600}\approx40$ AU). The method of the claimed invention, however, does not require this cell density and will work at both lower and higher cell concentrations.

Similarly, the method of the claimed invention does not require the use of any specific bioprocessor, but suitable laboratory scale bioprocessors useful for making small amounts of amphiphilic peptides by the present invention include the Braun Biostat E bench-scale fermentor with microprocessor-based control of pH, temperature and dissolved oxygen (B. Braun Biotech Inc., Allentown, Pa.) and the Trio Bioprocessing System of Sepracor Corporation (Marlborough, Mass.). Large-scale production of therapeutic amphiphilic peptides by the present claimed method necessitates using larger scale industrial fermentation equipment. The selection and optimization of such systems is well within the skill of those in this art.

Once established in a suitable bioprocessor, the transformed host cells are induced to express the carbohydrate binding protein portion/amphiphilic peptide fusion proteins of the claimed invention. As indicated above, expression refers to the actual synthesis of specific proteins on the basis of inherited or acquired genetic information. Thus, the carbohydrate binding protein portion/amphiphilic peptide fusion protein is expressed when the synthesis of the fusion protein can be demonstrated by techniques known to those of skill in this art. Such analytical techniques include but are not limited to polyacrylamide gel electrophoresis (PAGE).

As known by those skilled in this art, the regulated gene expression of the claimed invention is induced by use of controlling regulatory DNA sequences such as promoter and repressor gene segments. In one preferred embodiment, the *E. coli* promoter is the *E. coli* hybrid tac promoter. (DeBoer et al., *PNAS*, Vol. 80, pp. 21–25 (January 1983)). For example, the tac promoter controls the *E. coli* male gene encoding *E. coli* MBP in the pMal-2 vectors, operatively linked to DNA encoding the amphiphilic peptide or protein of the invention. In a preferred embodiment, the *E. coli* tac promoter includes a lac operator site for a lacI repressor. In another preferred embodiment, the *E. coli* promoter is the lac promoter. See J. H. Miller, *A Short Course in Bacterial Genetics* laboratory manual (Cold Spring Harbor Laboratory Press, N.Y. 1992), Unit 3.

The inducing agent is selected based on the regulatory sequence in the expression vector and then optimized for the system. For example, IPTG (isoproply-β-D-thiogalactoside) is an inducer of the lac operon in *E. coli* and, accordingly, is a preferred inducing agent for both the lac and tac promoters. Although a range of IPTG concentrations will successfully induce protein expression, in a preferred embodiment, IPTG is added at a final concentration between 50 and 400 μM and at the late stage of cell growth for full induction.

Other acceptable inducing agents include allolactose (in the form of lactose in the combined presence of the enzyme β-galactosidase in the growth media) and melibiose at effective concentrations determined empirically.

The expressed amphiphilic peptide is recovered from the protease-deficient host cell and then purified. When the peptide is expressed as a recombinant fusion protein partner, that partner may be used in the recovery and purification of the amphilic peptide.

When the host cell is transformed with a carbohydrate binding protein portion/amphiphilic peptide fusion proteins, the proteins are preferably expressed as soluble fusion proteins and then recovered and purified. In one embodiment, one step recovery and purification of the fusion protein is possible based on the affinity of the carbohydrate binding protein for maltose, amylose or other sugars to which the carbohydrate binding protein will bind. See Maina C. V. et al., in *Gene* 74, 365 (1988) and H. Bedouelle and P. Duplay, *Eur. J. Biochem.* 171, 541 (1988) for a discussion of such processes.

In one embodiment of the claimed invention, the host cell is lysed and a supernatant fraction is collected and subjected to affinity chromatography based on amylose, maltose, or other such carbohydrates. Affinity column resins, such as cross linked amylose or amylose-agarose conjugates, may either be purchased from New England Biolabs from Beverly, Mass. or Sigma Chemicals from St. Louis, Mo. or be individually prepared. The preparation and use of such resins or cross-linked materials is well within the routine skill of those practiced in the art.

In a preferred method, the portion of a carbohydrate binding protein is sufficient to allow binding of the carbohydrate binding protein portion/amphiphilic peptide fusion protein to a carbohydrate affinity matrix. In a particularly preferred method, prior to cleavage of the fusion protein, the carbohydrate binding protein portion/amphiphilic peptide fusion protein is bound to a carbohydrate affinity matrix in a buffered salt solution maintained at a pH in the range 7–9, the column is washed with the buffered salt solution maintained at a pH in the range 7–9, and the carbohydrate binding protein portion/amphiphilic peptide fusion protein is eluted in the buffered salt solution maintained at a pH in the range 7–9 which contains unbound and soluble carbohydrate at a concentration sufficient to displace the carbohydrate binding protein portion/amphiphilic peptide fusion protein. In an even more preferred embodiment, the carbohydrate binding protein portion is the male gene product of *E. coli*.

Preferably, after the fusion protein containing the amphiphilic peptides produced by the host bacterium is recovered and purified, it is processed to remove the non-amphiphilic and non-antimicrobial protein segments or domains. The scission and removal of such sections may be accomplished through any known chemical or enzymatic cleavages specific for peptide bonds. Chemical cleavages include, but are not limited to, those catalyzed by cyanogen bromide, hydroxylamine, 2-nitro-5-thiocyano-benzoic acid or acid cleavage. See R. L. Lundblad, *Chemical Reagents for Protein Modification* (CRC Press, Boca Raton, Fla.; 1991), Chapter 5. Enzymatic cleavages which may be employed include, but are not limited to, those catalyzed by trypsin, chymotrypsin, enterokinase, human Factor Xa, human Factor XIIa, or thrombin.

In one embodiment, the DNA encoding a portion of the fusion protein and immediately adjacent to the 5' terminus of the DNA encoding the amphiphilic peptide may include a codon for methionine to provide a cleavage site where one may easily chemically split the amphiphilic peptide from the portion of a carbohydrate binding protein using cyanogen bromide in a suitable acid. The amphiphilic peptide in this embodiment does not contain any methionine residues.

In a preferred embodiment, the cyanogen bromide is present in at least a molar equivalent to the total number of methionine residues present in the cleavage reaction mixture. In a more preferred embodiment, the cyanogen bromide is present in molar excess to the total number of methionine residues. In another more preferred embodiment, the cyanogen bromide is present in greater than a ten-fold molar excess with respect to the total number of methionine residues.

In another more preferred embodiment, the acid present in a cyanogen bromide cleavage reaction is formic acid and the concentration of formic acid is at least 70% on a volume-to-volume basis. In another more preferred embodiment, the acid present in a cyanogen bromide cleavage reaction is trifluoroacetic acid and the concentration of trifluoroacetic acid is at least 70% on a volume-to-volume basis. In a furthermore preferred embodiment, the acid present in a cyanogen bromide cleavage reaction is hydrochloric acid and the concentration of hydrochloric acid is in the range of 0.1–0.2M.

In another embodiment of the present method, the DNA encoding a portion of the fusion protein and immediately adjacent to the 5' terminus of the DNA encoding the amphiphilic peptide is a codon for asparagine and the first amino acid of the amphiphilic peptide is glycine. One may easily chemically split such an amphiphilic peptide from the said portion of a carbohydrate binding protein using hydroxylamine in a suitable buffer. The amphiphilic peptide in this embodiment does not contain any asparagine-glycine dipeptide sequences.

In a preferred embodiment, the hydroxylamine is present in at least a molar equivalent to the total number of asparagine-glycine amino acid pairs in the cleavage reaction mixture. In a more preferred embodiment, the hydroxylamine is present in molar excess to the total number of asparagine-glycine amino acid pairs in the cleavage reaction mixture. In another more preferred embodiment, the hydroxylamine is present in greater than a tenfold molar excess with respect to the total number of asparagine-glycine amino acid pairs.

In another embodiment, the buffer for hydroxylamine cleavage of carbohydrate binding protein portion/amphiphilic peptide fusion proteins includes 2M hydroxylamine and a buffer reagent such as Tris-HCl (Tris[hydroxymethyl]amino methane hydrochloride) or potassium carbonate present at a concentration of at least 100 mM and at a solution pH in the range of 9–11. In a preferred embodiment, the buffer for hydroxylamine cleavage of fusion proteins of the present method is 2M hydroxylamine, 200 mM potassium carbonate, pH 9. In another preferred embodiment, the buffer for hydroxylamine cleavage of fusion proteins of the present method is 2M hydroxylamine, 150 mM Tris-HCl, pH 9, 2M guanidine hydrochloride.

In another embodiment of the present method, the DNA encodes two or more amphiphilic peptides. In a preferred embodiment, the DNA encodes two amphiphilic peptides with a spacer peptide sequence joining them and the DNA of each amphiphilic peptide lacks codons for asparagine or cysteine and the first codon for each DNA encoding an amphiphilic peptide encodes glycine. In a more preferred embodiment, the DNA encoding a portion of the fusion protein and immediately adjacent to the 5' terminus of the DNA encoding the first amphiphilic peptide is a codon for asparagine, the first codon of DNA encoding a spacer peptide sequence is a codon for cysteine and the last codon of DNA encoding a spacer peptide sequence is a codon for aspargine.

One may easily chemically split such amphiphilic peptides from the fusion protein containing said portion of a carbohydrate binding protein using a combination of hydroxylamine and a cyanylating chemical agent such as 1-cyano-4-(dimethyamino) pyridinium tetrafluoroborate or 2-nitro-5-thiocyano-benzoic acid in a suitable buffer. In a preferred embodiment, the hydroxylamine is present in at least a molar equivalent to the total number of asparagine-glycine amino acid pairs and 2-nitro-5-thiocyano-benzoic acid is present in at least a molar equivalent to the total number of cysteine residues in the cleavage reaction mixture. In a more preferred embodiment, the hydroxylamine is present in molar excess to the total number of asparagine-glycine amino acid pairs and 2-nitro-5-thiocyano-benzoic acid is present in a molar excess to the total number of cysteine residues in the cleavage reaction mixture. In another more preferred embodiment, the hydroxylamine is present in greater than a tenfold molar excess with respect to the total number of asparagine-glycine amino acid pairs and 2-nitro-5-thiocyano-benzoic acid is present in greater than a fivefold molar excess to the total number of cysteine residues. In another more preferred embodiment, the DNA encoding at least one amphiphilic peptide lacks adjacent codons for the dipeptide sequences phenylalanine-serine or phenyalanine-threonine.

In another embodiment, the buffer for hydroxylamine plus 2-nitro-5-thiocyano-benzoic acid cleavage of carbohydrate binding protein portion/amphiphilic peptide fusion proteins includes at least 2M hydroxylamine and at least 2M guanidine hydrochloride in a buffer reagent such as Tris-HCl (Tris[hydroxymethyl]amino methane hydrochloride), Tris-acetate or potassium carbonate present at a concentration of at least 100 mM and at a solution pH in the range of 8–10.

In another embodiment of the present invention, peptides produced by the claimed method are post-translationally amidated with a peptidyl-glycine-α-amidating monooxygenase enzyme. In a preferred embodiment, the peptidyl-glycine α-amidating monooxygenase enzyme is isolated from rat medullary thyroid cells. In another preferred embodiment, the peptidyl-glycine α-amidating monooxygenase enzyme is isolated from the African clawed frog, $X.$ $laevis$. In still another preferred embodiment, the peptidyl-glycine α-amidating monooxygenase enzyme is isolated from a recombinant microbial host which has been genetically engineered to produce active enzyme from a gene encoding a natural α-amidating monooxygenase. In a more preferred embodiment, peptides produced by the claimed method are amidated with a recombinant peptidyl-glycine α-amidating monooxygenase enzyme derived from a gene for such enzyme originating from rat medullary thyroid cells.

In one embodiment of the present invention, peptides produced by the claimed method are esterified, i.e., converted in high yield to C-terminal methyl esters. Those of skill in this art are familiar with esterification methods available for such processes, as set forth in Peptide Synthesis, 2nd Ed. (M. Bodanszky et al., John Wiley and Sons, NY, N.Y.; 1076), pgs. 49–56. In a preferred embodiment, the esterification takes place in the presence of methanol and thionyl chloride. In a more preferred embodiment, the methanol is present in molar excess relative to the peptide. In an even more preferred embodiment, the methanol is present in molar excess relative to the peptide, and the methanol:thionyl chloride:peptide molar ratios are approximately 1.2:0.1:1.0.

The peptide methyl esters are subsequently converted to the corresponding peptide amides in the presence of ammonia without protection of lysine ε-amino or arginine guanidino side chain groups. In one embodiment of the invention, the ammonia is present during chemical amidation of the peptide methyl esters as a saturated solution in methanol. In another embodiment of the invention, the ammonia is chilled and refluxed as a liquid with the peptide methyl ester. In a preferred embodiment, the ammonia is present as a saturated solution in methanol and the methanol is present in at least molar excess to the peptide methyl ester. In a more preferred embodiment, the methanol is present in at least a 20-fold molar excess relative to the peptide methyl ester. In another more preferred embodiment, the methanol is present in at least a 50-fold molar excess relative to the peptide methyl ester.

The inventors intend that any combination of the above described elements of the present invention also are to be considered as part of the invention. For example, the expression vector of the present invention may encode a fusion protein containing a peptide sequence chemically cleavable with cyanogen bromide, contain at least one amphiphilic peptide and may also both lack a rop genetic element and be expressed in an ompT⁻ protease-deficient *E. coli* host strain.

The foregoing general description and the following detailed descriptions of practice of the present invention therefore are exemplary and explanatory only and are not restrictive of the invention as claimed.

EXAMPLE 1

Selection of Antimicrobial Peptides for Recombinant Expression

Certain antimicrobial peptides (the natural peptides Magainin 2 and Polyphemusin I and analogue peptides designated MSI-63, MSI-78, MSI-98, MSI-344 (SEQ ID NO: 4) and MSI-556 (SEQ ID NO: 6)) were synthesized chemically or, in the instance of Polyphemusin I, were isolated from natural sources to select potent and broadly-acting antimicrobial peptides for recombinant expression.

Polyphemusin I was isolated from 20 mL of washed, pooled *Limulus polyphemus* hemocytes (Limuli Laboratories, Cape May, N.J.) by a modification of the method described by K. Moore et al. (*J. Biol. Chem* 266, 19851–19857 (1991)). Ten mL of packed cells were pulverized in liquid nitrogen and then extracted with ten volumes 60% acetonitrile and 1% trifluoroacetic acid (TFA) at 4° C. for 24 hours. The extract was centrifuged at 6000 rpm for 20 minutes at 4° C. in a Beckman JA-17 rotor and the supernatant was lyophilized and then resuspended in 8 mL of 25% acetonitrile and 0.1% TFA. The supernatant was then loaded onto a 1.5×50 cm Bio-Gel P-30 (Bio-Rad, Richmond, Calif.) gel filtration column. Three mL fractions were collected and dried under vacuum and tested for antimicrobial activity after reconstitution as described below. Bioactive fractions were pooled and an equal volume of buffer A (10 mM ammonium acetate, pH 5.0, 20% acetonitrile) was added.

These fractions were further purified on a polyCATA ion exchange column (4.6×200 mm, 5 um, 300 Å; PolyLC Inc., Columbia, Md.) with a 0–80% gradient of buffer B (10 mM ammonium acetate, pH 5.0, 20% acetonitrile, 1.5M NaCl) in A over 30 minutes at a flow rate of 1 mL/minute. Fractions were collected at 1 minute intervals and dried under vacuum. Fractions were then resuspended in water and tested for antimicrobial bioactivity. Those fractions showing peak activity were pooled and desalted on a Waters C-18 reverse phase Sep-Pak cartridge (Millipore Corporation, Bedford, Mass.). Eluted fractions were dried under vacuum and resuspended in water.

Antibacterial susceptibility testing was performed using a microdilution broth assay according to the guidelines of the National Committee for Clinical Laboratory Standards (NCCLS) Document M7-A2 (NCCLS, 1990). For preparation of peptide stock solutions, the peptide powder as an acetate salt was weighed on an analytical balance and transferred to a polypropylene tube. Stock solutions were prepared at a concentration of 1.024 mg/mL (or, in the case of natural polyphemusin, 1.00 mg/mL) by dissolving the powder in autoclaved (121° C., 20 psi, 20 minutes) deionized water. The peptide solution was used immediately, stored for up to ten days at 4° C., or stored longterm at −70° C. in 1 mL aliquotes in polypropylene cryovials. Mueller-Hinton broth (MHB)(BBL® catalog number 11443) was used in microtiter plates for diluting peptide stock solutions and for diluting each bacterial inoculum. MHB 5 mL prepared tubes (BBL® catalog number 95834) were used to culture an overnight plate of bacteria to the logarithmic phase of growth for inoculating the microtiter plates.

The bacteria used in the antimicrobial susceptibility testing are the quality control reference strains *Staphylococcus aureus* ATCC 29213, *Escherichia coli* ATCC 25922, and *Pseudomonas aeruginosa* ATCC 27853. Inoculum for each reference strain was prepared by taking a sample of bacteria from a 16–20 hour plate culture and inoculating into 5 mL of MHB (BBL® catalog number 95834) to an absorbance reading of approximately 0.02 at 600 nm ($A_{600}$) on a Beckman DU®-64 spectrophotometer. The culture was incubated at 35°–37° C. with shaking in a New Brunswick incubator shaker (Model G25) and the growth monitored spectrophotometrically until it reached $A_{600}$ of approximately 0.6; this absorbance represented approximately $1\times10^8$ colony-forming units per milliliter (CFUs/mL).

The culture was then diluted to approximately $1\times10^6$ CFUs/mL in autoclaved MHB (BBL® catalog number 11443) to produce the parent inoculum. A sample of the parent inoculating culture was diluted in 3 mM phosphate buffer (pH 7.2) through a series of 1:10 dilutions and the $10^{-4}$ and $10^{-5}$ dilutions were plated, incubated overnight at 35°–37° C., and counted the next day to verify inoculum density. Microtiter plates (Corning manufacturer number 2585096) were prepared with the use of a Beckman Biomek® 1000 automated laboratory workstation in combination with manual techniques. The microtiter plate was filled with diluent broth using the Biomek® 1000 instrument. Peptide stock solution was manually added to the top drug well of the microtiter plate using a Rainin Pipetman®, Model P-200. The peptide was serially diluted in twofold dilutions using the Biomek® 1000 instrument. One hundred microliters of the standardized bacterial inoculum was added to every well of the microtiter plates (except the blanks) using an Eppendorf Repeater® Model 4780 pipet equipped with an Eppendorf 5 mL combitip (catalog number 22 26 130-4). All peptides were tested in duplicate. In addition to the test peptide, three standard peptides (Magainin 2, MSI-63, and MSI-98) and a non-treated growth control were included to validate the assay. The final concentrations of peptide solution in the microtiter wells ranged from 0.25 ug/mL to 256 ug/mL. The final concentration of bacteria in the microtiter wells was $1–5\times10^5$ CFUs/mL. The final solution volume in each well was 200 uL. The microtiter plates were incubated overnight (16–20 hours) at 35°–37° C. after preparation in a Precision mechanical convection oven incubator Model 30M.

The Minimum Inhibitory Concentration (MIC) was defined as the lowest concentration of peptide that completely inhibits growth of the organism. This value was determined using the unaided eye. In addition, for a permanent record, the absorbance at 630 nm was read on a Dynatech MR5000 Microplate Reader, Version 2.7, and a printed record was generated on an Epson LX800 dot-matrix printer.

TABLE I

| Peptide | Minimum Inhibitory Concentration (ug/mL) Test Organism: | | |
|---|---|---|---|
| | Staph. aureus | Pseudo. aeruginosa | E. coli |
| MSI-63 | 4–8 | 32–64 | 32 |

TABLE I-continued

| Peptide | Minimum Inhibitory Concentration (ug/mL) Test Organism: | | |
|---|---|---|---|
| | Staph. aureus | Pseudo. aeruginosa | E. coli |
| MSI-78 | 8–16 | 4–8 | 8 |
| MSI-98 | >256 | >256 | >256 |
| MSI-344 (SEQ ID NO: 4) | 64 | 8 | 2–8 |
| MSI-556 (SEQ ID NO: 6) | 16 | 4 | 4–16 |
| Native Magainin 2 | 256 | 256 | 64–128 |
| Native Polyphemusin | 25 | 6 | 25 |

Table I summarizes the MIC values obtained from antimicrobial susceptibility assays on several natural and synthetic antimicrobial peptides. The results indicate that the related unamidated antimicrobial peptides MSI-344 (SEQ ID NO: 27) and MSI-556 (SEQ ID NO.: 6) are broadly active against both gram-negative and gram-positive human pathogenic bacteria and are generally more potent than either of the natural antimicrobial peptides Magainin 2 or Polyphemusin, and are therefore good candidates for recombinant expression.

EXAMPLE 2

Cloning and Expression of DNA Encoding MSI-556 (SEQ ID NO. 33) in pMAL Expression System The pMAL fusion protein expression and purification system (New England Biolabs, Beverly, Mass.) is based upon the properties of the E. coli malE gene product, maltodextrin-binding protein or MBP (Guan et al., *Gene*, vol. 67, pgs. 21–30 (1987); Maina et al., *Gene*, vol. 74, pgs. 365–373 (1988)). MBP has a strong affinity for maltodextrins such as maltose or amylose which allows purification of fusion proteins using affinity chromatography. For protein expression, the pMAL-c2 vector employs the hybrid tac promoter (De Boer et al., *Proc. Natl. Acad. Sci.*, Vol. 80, 21–25, 1983) which confers a high level of gene transcription and is inducibly regulated by the lacI repressor. The pMAL-c2 cloning vector also has lacZ alpha-complementation screening capability for the easy identification of positive DNA inserts (Yanisch-Perron et al., *Gene*, vol. 33, pgs. 103–119 (1985)). The pMAL-c2 fusion protein system directs protein expression to the bacterial cell cytoplasm.

Gene constructions for a synthetic MSI-556 (SEQ ID NO: 33) gene to be inserted into the pMAL-c2 vector were performed by synthesis on an Applied Biosystems (Foster City, Calif.) model 392 oligonucleotide synthesizer of two complementary oligonucleotides having the following sequences when annealed:

(5000:1 molar ratio, oligonucleotide duplex:vector) to the pMAL-c2 vector which had been digested to completion with restriction enzymes EcoRI and PstI (New England Biolabs) and purified on low melting agarose (FMC Corporation, Rockland, Me.).

Cells of E. coli strain TB1 (obtained from New England Biolabs) were made competent with $CaCl_2$ and transformed with the ligated vector/oligonucleotide DNA (Johnston et al., *J. Biol. Chem.*, vol. 261, pgs. 4805–4811 (1986); J. Sambrook et al., *Molecular Cloning: A Laboratory Manual* (2nd edition), pgs. 1.74–1.84 (1989)). Ampicillin-resistant colonies were isolated and tested for inactivation of the lacZ gene on LB agar plates containing isopropyl-β-D-thiogalacto-pyranoside (IPTG) and X-Gal (5-bromo-4-chloro-3-indolyl-β-D-thiogalactopyranoside).

Plasmid DNA was isolated from several clones that were positive for lacZ inactivation (Birnboim et al., *Nucl. Acids Res.*, vol. 7, pgs. 1513–1523 (1979)) and then analyzed by restriction mapping. A BglII and AflII double restriction digest was performed which released an 800 bp fragment from positive clones; a unique AflII site present in the oligonucleotide insert was diagnostic for clones containing the insert. Those clones that contained a correct restriction fragment were then further characterized by PCR analysis and DNA sequencing (J. Sambrook et al., *Molecular Cloning: A Laboratory Manual* (2nd edition), pgs. 14.1–14.35 (1989); Murray, *Nucl. Acids Res.*, vol. 17, pg. 8889 (1989)). One clone designated TB1 (pMALc-556#2) was positive by all analytical techniques employed and was stored as a frozen glycerol stock to be used for all protein expression and purification experiments.

Plasmid stability was tested by growing an aliquot of the frozen glycerol stock in LB medium with 50 ug/mL ampicillin at 37° C. until mid-logarithmic growth and then plating dilutions of the cells on LB agar plates, on LB agar plates with 50 ug/mL ampicillin, and on LB plates with 50 ug/mL ampicillin with 0.5 mM IPTG. Results after overnight culture at 37° C. (16–20 hours) were growth of approximately equal numbers of colonies of TB1(pMALc-556#2) on the LB and LB+ampicillin agar plates, indicating that the plasmid was stable in the culture. No colonies were seen on the LB agar plates containing IPTG, suggesting that expression of the MBP fusion protein was inhibitory to colony formation and all cells containing the pMALc-556#2 plasmid also contained a functioning fusion protein expression cassette.

EXAMPLE 3

Expression of Fusion Protein Containing MSI-556 (SEQ ID NO: 33) and Preparation of MSI-556 Peptide (SEQ ID NO: 6) from TB1(pMALc-556#2)

Expression of the MBP-MSI-556 fusion protein for purposes of MSI-556 peptide (SEQ ID NO: 6) isolation was

```
5'- AA TTC ATG GGT ATC GGT AAA TTC CTG AAA AAA GCT AAG AAA TTC
3'  -  G TAC CCA TAG CCA TTT AAG GAC TTT TTT CGA TTC TTT AAG

GGT AAA GCT TTC GTA AAG ATC CTT AAG AAA GGT TAA TAA CTG CA -3'
CCA TTT CGA AAG CAT TTC TAG GAA TTC TTT CCA ATT ATT G  - 5'
```

These oligonucleotides (SEQ ID NO: 33) contain the entire coding sequence of MSI-556 peptide (SEQ ID NO: 6), an amino terminal ATG methionine codon (for potential cyanogen bromide cleavage), and EcoRI and PstI compatible sticky ends. The oligonucleotides were annealed and ligated performed by adding 0.25 mL of an overnight culture of TB1(pMALc-556#2) to 250 mL of LB medium with 50 ug/mL ampicillin and growing this culture at 37° C. with shaking. Cell density was measured by absorbance at 600 nm. When the $A_{600}$ value was approximately 0.5, IPTG was added to 0.5 mM from a 200 mM IPTG stock solution in water and the culture was grown for an additional two hours. The E. coli cell culture was then centrifuged in a Beckman model J2-21M high speed centrifuge at 4000 rpm for 20 minutes at 4° C. using a Beckman model JA-14 rotor. The cell pellet was resuspended in 12.5 mL of MBP column buffer (20 mM Tris-HCl, pH 7.4, 200 mM NaCl, 1 mM Na$_2$EDTA) containing protease inhibitors PMSF (1 mM), pepstatin (20 ug/mL) and leupeptin (20 ug/mL). The sample was stored overnight at −20° C.

To release the MBP-MSI-556 fusion protein from the frozen cells, the cell sample was thawed and sonicated on ice for 2–4 minutes using a Branson model 450 sonicator at an output setting of 4 and a 50% duty cycle. The sample then was centrifuged in a Beckman model J2-21M centrifuge at 9000 rpm for 30 minutes at 4° C. using a Beckman model JA-17 rotor. The supernatant fraction was recovered and diluted with column buffer fourfold and placed on ice. Affinity chromatography was then performed using an open top column packed with about 15 mL of amylose resin (New England Biolabs) as described by the manufacturer. The fusion protein was eluted from the amylose resin in MBP column buffer containing 10 mM maltose. Sixteen 3 mL fractions were collected and stored at 4° C. for further analysis. The presence of fusion protein in the eluant fractions was confirmed by SDS-polyacrylamide gel electrophoresis (SDS-PAGE) on 4–20% SDS-polyacrylamide (PA) gradient gels (Bio-Rad Laboratories, Hercules, Calif.). The resulting gels were stained in 0.1% Coomassie blue R-350 (Pharmacia Biotech, Piscataway, N.J.) in 30% methanol/ 10% glacial acetic acid in water and destained in 30% methanol/10% glacial acetic acid in water. The stained gels showed good induction of the MBP-MSI-556 (SEQ ID NO: 33) fusion protein (10–20% of observable total cellular protein) compared to samples of uninduced cells.

Fractions containing the major portion of eluted MBP-MSI-556 fusion protein were pooled and two volumes of ethanol were added. The ethanol solution was held one hour on ice and then spun 3500 rpm for 30 minutes at 4° C. in a Beckman model GPR centrifuge. The protein pellet was air dried and resuspended in 70% formic acid at a concentration of 2–4 mg/mL. Cyanogen bromide (CNBr) was added as a crystalline solid to a final concentration of greater than 1 mg/mL. In other experiments, CNBr was added at a concentration of 10 mg/mL to a 2 mg/mL protein solution in 70% formic acid, 0.2N HCl or 70% TFA in water. The protein sample with CNBr was then incubated overnight in the dark at room temperature. The entire sample was subsequently lyophilized and the pellet was washed with 0.1 mL of 100 mM Tris-HCl (pH 8.0), was briefly centrifuged and the remaining pellet was resuspended in 0.6M guanidine-HCl, 100 mM Tris-HCl (pH 8.0). Alternatively, the pellet could be washed with 0.1–0.2 mL of deionized water, redried under vacuum, and resuspended in 0.2–0.4 mL of deionized water.

EXAMPLE 4

Isolation and Analysis of Recombinant MSI-556 (SEQ ID NO: 33)

Detection of recombinant MSI-556 in CNBr cleavage reaction products was carried out on a Rainin Dynamax® HPLC system using an Applied Biosystems Aquapore C8 reverse phase column (300 Å particle size; 2.1×220 mm column). Elutions conditions were 0.1% TFA in water for buffer A, 0.08% TFA in acetonitrile for buffer B and a gradient of 2% to 60% buffer B in A over 30 minutes, with UV monitoring of the eluant at 220 nm and 254 nm.

Synthetic MSI-556 eluted at approximately 18.6 minutes under these conditions. The chromatographic result at 220 nm from the CNBr cleavage of affinity purified MBP-MSI-556 fusion protein revealed a complex pattern of elution peaks corresponding to the eight expected peptide fragments predicted from the primary sequence of the MBP-MSI-556 fusion protein as well as minor protein and peptide contaminants. A significant chromatographic peak was seen at about 18.6 minutes; this peak material was further characterized as authentic MSI-556 by co-elution with chemically synthesized authentic MSI-556 (SEQ ID NO: 6).

Fractions were collected from the HPLC analysis of CNBr-treated MBP-MSI-556 fusion protein samples and selected samples (including those containing portions of the 18.6 minute peak material) were further characterized by re-analysis using HPLC or analysis by capillary zonal electrophoresis. Both of these analytical methods suggested that the materials isolated at 18.6 minutes from the CNBr-treated MBP-MSI-556 fusion protein samples obtained with TB1 as the E. coli host strain was identical to synthetic MSI-556 (SEQ ID NO: 6).

A bacterial growth inhibition assay (M. Zasloff, Proc. Natl. Acad. Sci. (U.S.A.), vol. 84, pgs. 5449–5453 (1987)) was performed to determine if antimicrobial activity of the purified recombinant MSI-556 was similar to that seen with chemically synthesized MSI-556 (SEQ ID NO: 6). Small aliquots of recombinant MSI-556 and other HPLC fractions from the CNBr digest of MBP-MSI-556 fusion protein were spotted onto a lawn of E. coli ATCC strain 25922 grown on a half-strength trypticase soy broth agar plate containing 50 mM sodium fluoride. Results of bacterial lawn growth inhibition as judged visually showed that the purified recombinant MSI-556 at 0.4 ug/mL displayed significant antimicrobial activity that was qualitatively similar to that seen with chemically synthetic MSI-556 (SEQ ID NO: 6) while other HPLC fraction samples did not display activity.

EXAMPLE 5

Cloning and Expression of DNA Encoding MSI-344 (SEQ ID NO: 27) in pMALc Expression System Gene constructions for a synthetic MSI-344 (SEQ ID NO: 27) gene to be inserted into the pMAL-c2 vector were performed by synthesis on an Applied Biosystems (Foster City, Calif.) model 392 oligonucleotide synthesizer of two complementary oligonucleotides having the following sequences when annealed:

```
5'- AA TTC ATG GGT ATC GGT AAA TTC CTG AAA AAA GCT AAG AAA TTC
3' -    G TAC CCA TAG CCA TTT AAG GAC TTT TTT CGA TTC TTT AAG

GGT AAA GCT TTC GTA AAG ATC CTT AAG AAA TAA TAA GTG CA -3'
CCA TTT CGA AAG CAT TTC TAG GAA TTC TTT ATT ATT G  - 5'
```

These oligonucleotides (SEQ ID NO: 27) contain the entire coding sequence of MSI-344 peptide (SEQ ID NO: 4), an amino terminal ATG methionine codon (for potential cyanogen bromide cleavage), and EcoRI and PstI compatible sticky ends. The coding sequence for PstI has been altered so that successful insertion of the above synthetic gene sequence eliminates the unique PstI recognition site.

These oligonucleotides were annealed and ligated (300:1 molar ratio, oligonucleotide duplex:vector) to the pMAL-c2 vector which had been digested to completion with restriction enzymes EcoRI and PstI. The ligation mixture was counterselected by digestion with PstI and then microdialyzed against 0.1× TE buffer (1× TE buffer=10 mM Tris-HCl, pH 8.0, 1 mM Na₂EDTA) prior to transformation.

Cells of E. coli K12 strain DH5α (obtained from GIBCO/BRL, Bethesda, Md.) were made competent in 10% glycerol and 80 uL of competent cells were electroporated with 100 ng of ligated DNA using an E. coli gene pulser device (Bio-Rad Laboratories, Richmond, Calif.) as described by the manufacturer. Ampicillin-resistant colonies were then isolated on LB agar plates containing 50 ug/mL ampicillin and plasmid DNA was isolated from several clones by alkaline lysis (T. Maniatis et al., *Molecular Cloning*, pp. 368–369) using 10 mg/mL lysozyme in the lysis buffer.

The plasmid DNA was analyzed by restriction mapping with AflII and PstI to identify potentially positive clones. Four clones whose plasmid DNA cut with AflII but not PstI were further characterized by DNA sequencing. One clone was found to have a full-length synthetic gene insert; this clone was designated pMALc344/DH5α and the plasmid DNA harbored by this clone was designated pMALc344. The clone pMALc344/DH5α was stored as a frozen glycerol stock.

Plasmid DNA from pMALc344/DH5α was isolated by alkaline lysis with 10 mg/mL lysozyme in the lysis buffer and used for electroporation of UT400 cells (from B. Bachmann, E. coli Genetic Stock Center, Yale University) prepared and transformed as described above. Positive transformant clones were isolated on LB agar plates containing 50 ug/mL ampicillin and plasmid DNA was isolated from several clones. The plasmid DNA was analyzed by restriction mapping with AflII and PstI to identify potentially positive clones. Two clones whose plasmid DNA cut with AflII but not PstI were further characterized by DNA sequencing. One clone was found to have a full-length synthetic gene insert; this clone was designated pMALc344/UT400 and was stored as a frozen glycerol stock to be used for all protein expression and purification experiments.

EXAMPLE 6

Expression of Fusion Protein Containing MSI-344 and Preparation of MSI-344 Peptide (SEQ ID NO: 4) from pMALc344/UT400

Expression of the MBP-MSI-344 fusion protein for purposes of MSI-344 peptide (SEQ ID NO: 4) isolation was performed by adding 3.0 mL of an overnight culture of pMALc344/UT400 to 500 mL of LB medium with 50 ug/mL ampicillin and growing this culture at 37° C. with shaking. Cell density was measured by absorbance at 600 nm. When the $A_{600}$ value was approximately 0.5, IPTG was added to 0.4 mM from a 100 mM IPTG stock solution in water and the culture was grown for an additional three hours. The E. coli cell culture was then centrifuged in a Beckman model J2-21M high speed centrifuge at 5800 rpm for 10 minutes at 4° C. using a Beckman model JA-14 rotor. The cell pellet was resuspended in 30 mL of MBP column buffer (20 mM Tris-HCl, pH 7.4, 200 mM NaCl, 1 mM Na₂EDTA) and the sample was stored overnight at −20° C.

To release the MBP-MSI-344 fusion protein from the frozen cells, the cell sample was thawed and sonicated on ice three times for 2 minutes using a Branson model 450 sonicator (Branson Ultrasonics Corporation, Danbury, Conn.) at an output setting of 5 and a 50% duty cycle. The sample then was centrifuged in a Beckman model J2-21M centrifuge at 9000 rpm for 30 minutes at 4° C. using a Beckman model JA-17 rotor. The supernatant fraction was recovered and diluted with column buffer fourfold and placed on ice. Affinity chromatography was then performed using an open top column packed with about 17 mL of amylose resin (New England Biolabs) as described by the manufacturer. The fusion protein was eluted from the amylose resin in MBP column buffer containing 10 mM maltose. Ten 5 mL fractions were collected and stored at 4° C. for further analysis. The presence of fusion protein in the eluant fractions was confirmed by SDS-polyacrylamide gel electrophoresis (SDS-PAGE) on 10% Daiichi SDS-polyacrylamide (PA) Multigels (Integrated Separation Systems, Natick, Mass.). The resulting gels were stained in 0.1% Coomassie blue R-350 (Pharmacia) in 30% methanol/10% glacial acetic acid in water and destained in 30% methanol/10% glacial acetic acid in water.

Fractions containing the major portion of eluted MBP-MSI-344 fusion protein were analyzed for protein content using a BCA protein assay reagent (Pierce Chemical Company, Rockford, Ill.) and pooled. Two volumes of ethanol were added to about 2 mg of fusion protein and the ethanol solution was held one hour on ice before it was spun 3500 rpm for 30 minutes at 4° C. in a Beckman model GPR centrifuge. The protein pellet was air dried and resuspended in 70% formic acid or 70% trifluoroacetic acid (TFA) in water at a concentration of 2 mg/mL. Cyanogen bromide (CNBr) was added from a 1 gm/mL solution in TFA to a final concentration of 10 mg/mL. The protein sample with CNBr was then incubated overnight in the dark at room temperature. The entire sample was subsequently lyophilized and the pellet was washed with 0.2 mL of deionized water. The sample then was briefly centrifuged and the remaining pellet was redried under vacuum before it was resuspended in 0.4 mL of deionized water.

EXAMPLE 7

Isolation and Analysis of Recombinant MSI-344 (SEQ ID NO: 27)

Detection of recombinant MSI-344 in CNBr cleavage reaction products was carried out on a Rainin Dynamax® HPLC system using an Applied Biosystems Aquapore C8 reverse phase column (300 Å particle size; 2.1×220 mm column). Elution conditions were 0.1% TFA in water for buffer A, 0.08% TFA in acetonitrile for buffer B and a gradient of 2% to 60% buffer B in A over 30 minutes, with UV monitoring of the eluant at 220 nm and 254 nm. Synthetic MSI-344 (SEQ ID NO: 4) eluted at approximately 18.9 minutes under these conditions. The chromatographic result at 220 nm from the CNBr cleavage of affinity purified MBP-MSI-344 fusion protein revealed a significant chromatographic peak at 18.6–19.1 minutes. Fractions were collected from the HPLC analysis of CNBr-treated MBP-MSI-344 fusion protein samples and selected sample fractions (including those containing portions of the 18.6–19.1 minute peak material) were further characterized by bioassay and analysis by capillary zonal electrophoresis.

The bacterial growth inhibition assay performed as described in Example 4 revealed antimicrobial activity in HPLC fractions taken over an 18.5–19.5 minute elution time period while adjacent time period HPLC fraction samples did not display activity. Capillary zonal electrophoresis on the same HPLC fractions was carried out on an Applied Biosystems model 270A capillary electrophoresis unit equipped with an Applied Biosystems model HT autosampler. Electrophoretic conditions were a 3 second electrokinetic injection of sample with electrophoresis at 45° C. in 77 mM sodium phosphate buffer, pH 2.5; field strength was 25 kV. Chemically synthesized MSI-344 peptide (SEQ ID NO: 4) provided an electropherogram with a single peak at an elution time of 5.9 minutes. HPLC purified peak material collected from CNBr-treated MBP-MSI-344 fusion protein over the time period 19–19.5 minutes displayed on capillary zonal electrophoresis a single peak at an elution time of 6.0 minutes; adjacent HPLC time period fractions showed no such peak. This result was consistent with the presence of recombinant MSI-344 (SEQ ID NO: 4).

Additional confirming evidence for the presence of recombinant MSI-344 peptide (SEQ ID NO: 4) in the MBP-MSI-344 fusion protein isolated by affinity chromatography on amylose resin as described in Example 6 was obtained by amino acid analysis of the fusion protein. Amino acid analysis was carried out on an Applied Biosystems amino acid analyzer equipped with a 420A derivatizer, an 130A separation system and a 920A data module. Analyses were carried out in triplicate on samples which were hydrolyzed in 6N HCl and derivatized with phenylthioisocyanate (PITC). PITC-derivatized amino acids were separated on an Applied Biosystems C18-PITC column (5 um particle size; 2.1×220 mm column) at 45° C., 300 uL/minute solvent flow rate. Elution conditions were 50 mM sodium acetate, pH 5.4, for buffer A, 32 mM sodium acetate in 70% acetonitrile in water for buffer B and a gradient of 6–16% buffer B in A over 4 minutes, followed by a gradient of 16–32% B in A over 6 minutes and finally a gradient of 32–60% B in A over 10 minutes, with UV monitoring of the eluant at 254 nm. The relative amino acid content results for MBP-MSI-344 fusion protein (Table II below) suggest that the fusion protein was at least 90% pure and are consistent with the presence of MSI-344 peptide (SEQ ID NO: 4) in the fusion protein.

TABLE II

| Amino Acid | Number of Amino Acid Residues | |
|---|---|---|
| | Expected | Observed* |
| Aspartic Acid + Asparagine | 55 | 57 |

TABLE II-continued

| Amino Acid | Number of Amino Acid Residues | |
|---|---|---|
| | Expected | Observed* |
| Glutamic Acid + Glutamine | 38 | 39 |
| Serine | 16 | 18 |
| Glycine** | 34 | 81 |
| Histidine | 3 | 4 |
| Arginine | 6 | 6 |
| Threonine | 19 | 29 |
| Alanine | 46 | 48 |
| Proline | 21 | 23 |
| Tyrosine | 15 | 13 |
| Valine | 21 | 23 |
| Methionine | 8 | 7 |
| Isoleucine | 26 | 28 |
| Leucine | 33 | 34 |
| Phenylalanine | 20 | 20 |
| Lysine | 45 | 42 |
| Tryptophan | 8 | *** |

* = Observed values are normalized for 20 phenylalanine residues
** = Artifacually high value, probably related to the presence of dust
*** = Tryptophan not detectable due to decomposition during acid hydrolysis Mass spectrometry on HPLC-purified MBP-MSI-344 fusion protein and recombinant MSI-344 peptide (SEQ ID NO: 4) provided additional supporting evidence that the recombinant clone pMALc344/UT400 synthesizes MSI-344 (SEQ ID NO: 4) within the presumed MBP-MSI-344 fusion protein. About 4 ug of purified recombinant MSI-344 peptide (SEQ ID NO: 4) was analyzed by electrospray mass spectrometry at M Scan (West Chester, Pa.) using a VG Biotech BIO-Q instrument with quadrupole analyzer. When deconvoluted, the data showed a single major component at 2477.8 daltons, which is very close to the calculated molecular mass of 2478.2 for authentic MSI-344 peptide (SEQ ID NO: 4). Matrix-assisted laser desorption/ionization time-of-flight mass spectrometric analysis of HPLC-purified MBP-MSI-344 fusion protein was conducted on a VESTEC-2000 instrument at the University of Michigan Biomedical Research Core Facility (Ann Arbor, Mich.) using myoglobin (molecular mass 16,952 daltons) as an internal standard. The HPLC-purified MBP-MSI-344 fusion protein mass was measured as 45,538 daltons, which is in error by less than 0.1% from the expected fusion protein mass of 45,582 daltons.

EXAMPLE 8

Comparison of MBP-MSI-344 fusion protein and MSI-344 peptide (SEQ ID NO: 4) expression in *E. coli* strains DH5α, AB1899, RW193, TB1 and UT400

A comparison of the suitability of a series of *E. coli* host strains for producing MBP-MSI-344 fusion protein and MSI-344 peptide (SEQ ID NO: 4) was carried out. The *E. coli* K-12 strains studied are listed, with their genotypes, in Table III, below. The host strain TB1 is supplied by New England Biolabs with their plasmid expression vector pMAL-c2, while DH5α is a common gene cloning and expression host. The paired strains RW193 and UT400 differ only in the protease ompT⁻ characteristic of UT400. AB1899 is a lon⁻ mutant.

TABLE III

| E. coli Strain | Genotype | Reference |
|---|---|---|
| AB1899 | F−, thr-1, ara-14, leuB6, Δ(gpt-proA)62, lacY1, tsx-33, lon-1, supE44, galK2, λ−, rac− hisG4, rfbD1, rpsL31, kdgK51, xyl-5, mtl-1, argE3, thi-1 | 1 |
| DH5α | F− φ80dlacZΔM15 Δ(lacZYA-argF)U169 deoR recA1 endA1 hsdR17($r_k^-$, $m_k^+$) supE44 λ thi-1 gyrA96 relA1 | 2 |
| RW193 | F−, purE+, entA−, tonA+ derivative of AB1515 | 3 |
| TB1 | hdsR ($r_k^-$, $m_k^+$), F− ara Δ(lac-proAB) rpsL (Str$^r$) [φ80 dlacΔ(lacZ)M15] | 4 |
| UT400 | spontaneous fepA mutant of RW193; ara-14, leuB6, azi-6, lacY1, proC14, tsx-67, Δ(ompT-fepC)267, entA403, λ−, trpE38, rfbD1, rpsL109, xyl-5, mtl-1, thi-1 | 3 |

Table references:
1. P. Howard-Flanders et al., Genetics 49, 237–??? (1964); P. Howard-Flanders et al., Genetics 53, 1119–??? (1966)
2. D. Hanahan, J. Mol, Biol. 166, 557–?? (1983); 1993–1994 catalogue for GibcoBRL Life Technologies (Bethesda, MD).
3. M. A. McIntosh et al., J. Bacteriol. 137, 653–657 (1979).
4. T. A. Baker et al., Proc. Natl. Acad. Sci. (U.S.A.) 81, 6779–6783 (1984).

About 10 ng plasmid DNA from the clone pMALc344/UT400 described in Example 5 was electroporated into each of E. coli strains AB1899, DH5α, RW193 and TB1 using an E. coli pulser device (Bio-Rad Laboratories) and ampicillin-resistant colonies were then isolated on LB agar plates containing 50 ug/mL ampicillin. Positive clones bearing the plasmid pMALc344 were identified by restriction mapping with the restriction enzymes AflII and PstI and/or PCR analysis.

A 5.0 mL overnight positive clone culture for each host was then grown in LB medium with 50 ug/mL ampicillin and diluted the next morning into about 500 mL LB medium with 50 ug/mL ampicillin. The cultures were then induced with IPTG as described in Example 6. The induced cultures were subsequently grown with aeration at 37° C. for 3–4 hours before the cell culture was harvested and disrupted as described in Example 6. The final $A_{600}$ value for these cultures ranged from $A_{600}$=1.3 (pMALc344/DH5α) to 3.0 (pMALc344/RW193).

Figure 2:
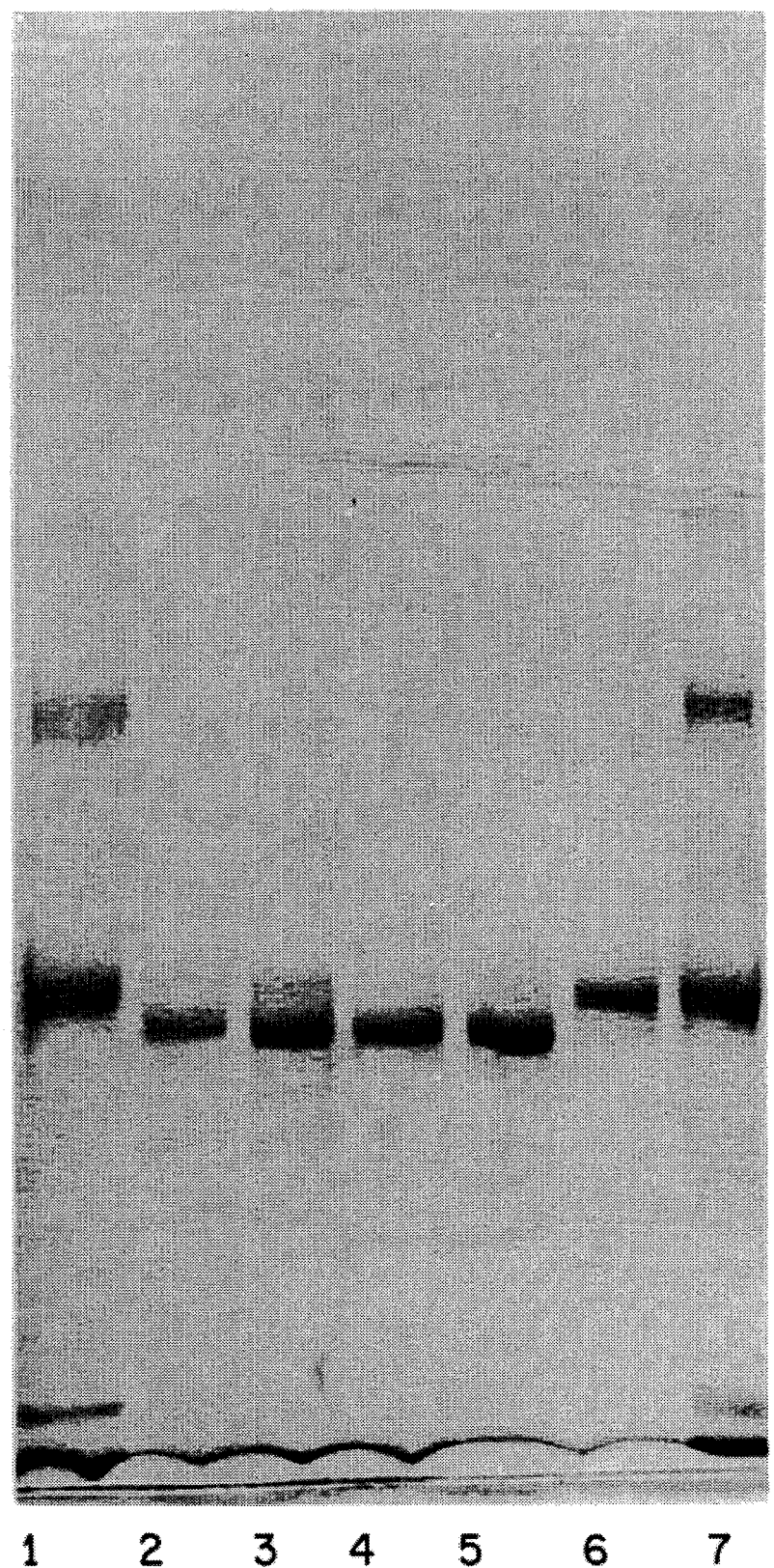
FIG. 2 is an SDS-PAGE gel separation of malE-MSI-344 (SEQ ID No. 4) fusion protein isolated from several E. coli protease-proficient or protease deficient host cell strains. Lanes 1 and 7: high range protein molecular weight markers (GIBCO BRL/Life Technologies, Inc.); Lane 2: E. coli DH5α host strain; Lane 3: E. coli RW193 host strain; Lane 4: E. coli TB1 host strain; Lane 5: E. coli AB1899 host strain; Lane 6: E. coli UT400 host strain.

Fusion protein was isolated from the cell lysates as described in Example 6. The final fusion protein yield for the peak protein fractions from affinity chromatography for these five cultures as judged by SDS-PAGE gel electrophoresis and BCA protein content assay ranged from 4.2 mg (from pMALc344/TB1) to 15.0 mg (from pMALc344/UT400) for the parent 500 mL culture. Side-by-side SDS-PAGE gel electrophoresis carried out as described in Example 6 for 3 ug of each affinity purified-fusion protein revealed that the largest, presumably non-degraded, fusion protein band was most prominent for fusion protein from the protease-deficient (ompT−) pMALc344/UT400 culture (FIG. 2). By contrast, little or none of the non-degraded fusion protein band was seen for fusion protein isolated from the protease-proficient pMALc344/DH5α culture. The other three cultures, including the culture with the protease-deficient (lon−) strain AB1899 as host cell, showed both apparent full-length fusion protein and one or two slightly smaller prominent protein bands that may represent partially degraded fusion protein.

Further support for the stability of pMALc344-encoded fusion protein in the protease-deficient E. coli host UT400 in comparison to the other E. coli hosts listed above was provided by additional purification of affinity-purified MBP-MSI-344 fusion protein, or, in the case of the E. coli host UT400, both MBP-MSI-344 and MBP-MSI-556 fusion protein on reverse phase HPLC with a Rainin Dynamax® HPLC system using an Applied Biosystems Aquapore C8 reverse phase column (300 A particle size; 2.1×220 mm column) and subsequent matrix-assisted laser desorption/ionization time-of-flight (MALD/ITOF) mass spectrometric analysis on HPLC-purified MBP-MSI-344 fusion protein. HPLC elution conditions were 0.1% TFA in water for buffer A, 0.08% TFA in acetonitrile for buffer B and a gradient of 2% to 30% buffer B in A over 10 minutes, followed by a gradient of 30% to 60% buffer B in A over 60 minutes, with UV monitoring of the eluant at 220 nm and 254 nm.

MBP-MSI-344 fusion protein peak material eluted during the 37–40 minute time interval, or about 43–47% buffer B in A. It was noted that the MBP-MSI-344 and MBP-MSI-556 fusion protein peak material was a unitary peak only for fusion protein isolated from the host UT400. With all other E. coli hosts tested, the HPLC-purified MBP-MSI-344 fusion protein peak material chromatograms displayed two or three major closely-spaced peaks over the 37–40 minute time interval. MALD/ITOF mass spectrometry was conducted on purified fusion protein on a VESTEC-2000 instrument at the University of Michigan Biomedical Research Core Facility (Ann Arbor, Mich.) using myoglobin (molecular mass 16,952 daltons) as an internal standard. The major fusion protein molecular masses detected with the various E. coli hosts are listed in Table IV below. The molecular mass data suggest that there is significant degradation of fusion protein MBP-MSI-344 fusion protein in all E. coli hosts other than UT400.

TABLE IV

| E. coli Host | Plasmid* | Molecular Mass (daltons) | | Mass Error (%)** |
|---|---|---|---|---|
| | | Expected | Actual | |
| UT400 | pMALc344 | 45,582 | 45,626 | +0.1% |
| | pMALc556 | 45,639 | 46,200 | +1.2 |
| AB1899 | pMALc344 | 45,582 | 43,772 | −4.0 |
| TB1 | pMALc344 | 45,582 | 43,773 | −4.0 |
| RW193 | pMALc344 | 45,582 | 43,772 | −4.0 |

TABLE IV-continued

| E. coli Host | Plasmid* | Molecular Mass (daltons) | | Mass Error (%)** |
| --- | --- | --- | --- | --- |
| | | Expected | Actual | |
| | | | 43,067 | −5.6 |
| | | | 40,628 | −10.9 |
| DH5α | pMALc344 | 45,582 | 44,156 | −3.1% |

\* = pMALc344 encodes the fusion protein MBP-MSI-344 and pMALc445 encodes the fusion protein MBP-MSI-556
\*\* = The percent mass error is calculated as [(actual mass − expected mass)/expected mass]

Further supporting evidence for potential degradation of MBP fusion protein in various *E. coli* host strains was obtained by ethanol precipitating 1 or 2 mg of affinity-purified fusion protein and treating the protein precipitate with CNBr in 70% trifluoroacetic acid for 15–20 hours as described in Example 6. The CNBr reaction mixtures were then dried, rinsed in 0.2 mL distilled water, redried and resuspended in 400 uL 10% acetonitrile in water prior to reverse phase HPLC analysis as described in Example 7. HPLC chromatographic peak profiles over the 17–20 minute time period revealed a peak eluting at about 18.6–18.9 minutes in all CNBr digests except for CNBr-treated MBP-MSI-344 fusion protein isolated from the *E. coli* host DH5α; the observed 18.6–18.9 peak materials coeluted with chemically synthesized MSI-344 peptide (SEQ ID NO: 4) in separate experiments. Bioassays conducted as described in Example 7 for HPLC fractions isolated during the 17.5–19.5 minute time period were positive for fractions from all fusion protein CNBr digests except for digests of fusion protein from pMALc344/DH5α.

Bioactive fractions (or, in the instance of CnBr-treated fusion protein from pMALc344/DH5α, HPLC fractions from the 18.5–19.5 minute time period) were pooled, reduced in volume to under 200 uL vacuum using a Savant (Farmingdale, N.Y.) SC100 Speedvac® concentrator with an RT100 condensation trap, and analyzed by fast atom bombardment mass spectrometry (FAB-MS) (for CNBr-treated fusion protein from *E. coli* hosts DH5α or UT400) at M Scan (West Chester, Pa.), by MALD/ITOF mass spectrometry (for CnBr-treated fusion protein from *E. coli* hosts DH5α, RW193, TB1, AB1899 or UT400) at the University of Michigan's protein structure facility (Ann Arbor, Mich.), or by electrospray mass spectrometry (for CNBr-treated fusion protein from *E. coli* hosts UT400, TB1 or AB1899) either at M Scan (West Chester, Pa.) or at the University of Michigan protein structure facility (Ann Arbor, Mich.). The observed molecular masses [m/(z=+1)] of major ion clusters (Table V) confirm the presence of MSI-344 peptide (SEQ ID NO: 4; calculated molecular mass 2477 daltons) in all samples except that from DH5α as a recombinant host strain. This result suggests that any observed MSI-344 peptide (SEQ ID NO: 4) or fusion protein degradation seen in the *E. coli* host strains tested is not complete, although DH5α does degrade almost all MSI-344 peptide (SEQ ID NO: 4) contained in amylose-purified fusion protein. This latter observation is based upon noting for DH5α that the molecular ion mass m+1 of 2478 daltons corresponding to MSI-344 peptide (SEQ ID NO: 4) is present only as a minor species, and is undetectable with α-cyanosinapinic acid as an alternative mass spectrometry matrix (data not shown).

TABLE V

| E. coli Host Strain | Major Quasi-Molecular Ion Cluster(s) Molecular Mass: | | | Minor Ion Clusters |
| --- | --- | --- | --- | --- |
| | [m + 1] [m + 1/(z = −1)] | | $m_r$ | |
| | Method: | | | |
| | LD-MS* | FAB-MS | Electrospray | LD-MS** |
| DH5α | 550 | 601, 904 | | 2479 |
| | | | | 5942 |
| RW193 | 2501*** | | | |
| | 2524*** | | | |
| TB1 | 2476 | | 2476 | |
| | 2498*** | | | |
| AB1899 | 2479 | | 2477 | |
| UT400 | 2472 | | 2478 | 5735 |
| | | | | 5931 |
| | | | | 6200 |

\* = the assisting matrix was α-cyanosinapinic acid for these LD-MS observations.
\*\* = the assisting matrix was sinapinic acid for these LD-MS observations.
\*\*\* = molecular complex with one or two sodium atoms.

EXAMPLE 9

Cloning and Gene Expression of Recombinant Lim1 fusion protein and Isolation of recombinant Lim1

The general applicability of the present invention was affirmed by cloning and expressing an antimicrobial peptide gene unrelated to MSI-344 or MSI-556. Gene constructions for a synthetic Lim1 gene (SEQ ID NO: 39) to be inserted into the pMAL-c2 vector were performed by synthesis on an Applied Biosystems (Foster City, Calif.) model 392 oligonucleotide synthesizer of two complementary oligonucleotides having the following sequences:

```
5'- AA TTC ATG CGT CGC TGG TGT TTC CGC GTC TGC TAC CGT GGC TTC TGT TAT
 3' -  G TAC GCA GCG ACC ACA AAG GCG CAG ACG ATG GCA CCG AAG ACA ATA

CGT AAA TGC CGT GGT TAA TAA CTT A - 3'
    GCA TTT ACG GCA CCA ATT ATT GAA TTC GA - 5'
```

These oligonucleotides (SEQ ID NO: 39) encode a peptide equivalent to the amino acid sequence of native Polyphemusin I with an extra C-terminal glycine; the glycine residue was added since it can be converted enzymatically to an amide group (M. Tajima et al., *J. Biol. Chem.* 265, 9602–9605 (1990); M. V. L. Ray et al. *Bio/Technology* 11, 64–70 (1993)) to yield a peptide equivalent to native Polyphemusin I. The above oligonucleotides were used directly after deprotection without further purification and were annealed at 70° C. The cloning vector pMAL-c2 was digested with restriction enzymes EcoR1 and HindIII (New England Biolabs), purified on low melting point agarose and then ligated to the annealed oligonucleotides as described in Example 2. The ligation mixture was subsequently transformed into E. coli K-12 strain UT400 and positive transformants were identified as detailed in Example 2. The DNA sequence of the clone MalE-Lim1 (MalE-rLim1) fusion gene endpoints was confirmed by the double stranded, cycle sequencing method (V. Murray, Nucleic Acids Res. 17, 8889–(1989)) using a dsDNA cycle sequencing system kit (GibcoBRL/Life Technologies, Inc., Bethesda, Md.).

Expression and purification of MalE-rLim1 fusion protein was carried out essentially as described in Example 3. Affinity-purified MalE-rLim1 fusion protein isolated from 500 mL of induced recombinant culture was treated in the dark with CNBr at a final concentration of about 1 mg/mL in 2 mL 70% formic acid in water for 16–20 hours. The sample was then dried under vacuum and stored at 4° C. until further purification was carried out. The cleavage pellet was resuspended in 0.5 mL of 10 mM ammonium acetate, pH 5.0, in 20% acetonitrile in water for purification and analytical procedures.

The CNBr reaction mixture was applied to a weak cation exchange HPLC column (polyCATA, PolyLC Inc., Columbia, Md.; 300 Å, 5 um, 4.6×200 mm) and eluted with a gradient of 0–80% buffer B in A over 30 minutes at a flow rate of 1 mL/minute, where buffer A was 10 mM ammonium acetate, pH 5.0, 20% acetonitrile in water and buffer B was 10 mM ammonium acetate, pH 5.0, 20% acetonitrile and 1.5M NaCl in water. Fractions were collected at 1 minute intervals and dried under vacuum, then resuspended in water and tested for antimicrobial activity as described in Example 1. Bioactive fractions were observed without the need for refolding the peptide despite the presence of two disulfide bridges in native Polyphemusin I (M. Ohta et al., Antimicro. Agents and Chemother. 36, 1460–1465 (1992)).

Fractions displaying peak antimicrobial activity were pooled and desalted on a Waters C-18 reverse phase Sep-Pak cartridge (Millipore Corporation, Bedford, Mass.). Eluted fractions were dried under vacuum, resuspended in water and subsequently subjected to analysis by reverse phase HPLC as described in Example 4. Approximately 100 ug of HPLC-purified recombinant Lim1 (SEQ ID NO: 8) were recovered from 50 mg of MalE-rLim1 fusion protein.

The HPLC-purified recombinant Lim1 peptide (SEQ ID NO: 8) was also found to be bioactive as determined in an antimicrobial susceptibility assay carried out as described in Example 1 without the need for careful reformation of the two disulfide bridges. A portion of recombinant Lim1 peptide (SEQ ID NO: 8) and native Polyphemusin I prepared as described in Example 1 were analyzed on a native acid polyacrylamide electrophoretic gel (N. Resnick et al., Cell 66, 541–554 (1991) and found to have very similar migration patterns, migrating as single bands under these conditions. Amino acid analysis of recombinant Lim1 peptide (SEQ ID NO: 8) (Table VI) provided evidence of the purity and identity of this antimicrobial peptide sample as recombinant Lim1 peptide (SEQ ID NO: 8), including the presence of the expected extra glycine residue.

TABLE VI

| Amino Acid | Number of Amino Acid Residues | |
|---|---|---|
| | Expected | Observed* |
| Glycine | 2 | 2 |
| Arginine | 6 | 5 |
| Tyrosine | 2 | 1.5 |
| Valine | 1 | 1 |

TABLE VI-continued

| Amino Acid | Number of Amino Acid Residues | |
|---|---|---|
| | Expected | Observed* |
| Phenylalanine | 2 | 2 |
| Lysine | 1 | 1 |
| Cysteine | 4 | 3 |
| Tryptophan | 1 | ** |

* = Observed values are normalized for 2 phenylalanine residues
** = Tryptophan not detectable due to decomposition during acid hydrolysis Matrix-assisted laser desorption/ionization time-of-flight (MALD/ITOF) mass spectrometric analysis on HPLC-purified recombinant Lim1 peptide (SEQ ID NO: 8) carried out at the University of Michigan protein structure facility (Ann Arbor, Mich.) revealed a molecular mass of 2512.2 daltons, equivalent to the expected molecular mass of 2512.2 daltons if both disulfide bonds have formed in the molecule.

EXAMPLE 10

Cleavage of MSI-344 Peptide (SEQ ID NO: 4) from Fusion Protein with Hydroxylamine Maltose binding protein/MSI-344 fusion protein was expressed in E. coli and affinity purified as described in Example 6. Affinity column fractions containing protein were concentrated and desalted by ultrafiltration with Centricon-10 devices (Amicon, Inc., Beverly, Mass.). The samples were placed in the Centricon devices and spun in a Beckman J2-21M centrifuge (JA-17 rotor) at 5000 g for 2–3 hours to achieve an approximately ten-fold volume reduction. The samples were then reconstituted to their original volume with distilled water and subjected to a second round of ultrafiltration in order to concentrate the protein and reduce sample salt concentration.

An aliquot of the concentrated fusion protein containing 2 mg of protein was then added to 1.75 mL of a solution containing 2.3M hydroxylamine, 2.3M guanidine hydrochloride, and 171.5 mM Tris buffer (adjusted to pH 9.0 with 4.5M lithium hydroxide). The volume of the reaction was then brought to 2 mL with distilled water and the pH was readjusted to 9.0 with lithium hydroxide. This resulted in final reaction conditions of 2M hydroxylamine, 2M guanidine hydrochloride, 150 mM Tris buffer (pH 9.0), and 1 mg/mL fusion protein.

The reaction mixture was incubated in a closed tube at 45° C. for 48 hours. The reaction was stopped by passage of the reaction mixture through a G-25 desalting column equilibrated in distilled water. The G-25 fractions were then dried in a Savant-Vac concentrator (Savant Instruments, Inc., Farmingdale, N.Y.). Fractions containing released MSI-344 peptide (SEQ ID NO: 4) were identified using a bioassay and were further analyzed by reverse phase HPLC as described in Example 7. These conditions resulted in production of bioactive MSI-344 peptide (SEQ ID NO: 4) with a cleavage efficiency of approximately 20%.

EXAMPLE 11

Improving Fusion Protein Expression by Deletion of the rop Locus from the pMALc344 Expression Vector A rop⁻ version of the pMALc344 expression vector (designated pMALc344 (rop⁻)) was constructed and cloned by excision of the rop locus on a Bst 1107 I/Msc I double-restriction enzyme digest fragment from the plasmid pMALc344 described in Example 5, agarose gel purification of the remaining vector sequences, recircularization by blunt ended ligation, and electroporation into E. coli strain UT400. Elimination of the smaller unique Bst 1107 I/Msc I DNA fragment was confirmed by restriction mapping with the enzymes AccI, HindIII, BamHI and EcoRI.

The plasmid yields from parallel cultures of UT400 clones containing pMALc344 with or without the rop locus were compared to determine whether removal of the negative copy number control rop element resulted in increased plasmid production. Plasmid copy number of pMALc344(rop⁻) was five to ten times greater than that of the rop⁺ version based on the intensity of ethidium bromide staining of linearized DNA samples derived from equal numbers of cells and separated on 1% agarose gels by electrophoresis using standard techniques.

Increased production of fusion protein from a clone containing the pMALc344(rop⁻) plasmid relative to a clone containing the rop⁺ parent construct was demonstrated by comparing fusion protein levels in induced cultures. Parallel cultures were induced with 0.4 mM IPTG at an $OD_{600}$ of 0.8 and aliquots were removed for analysis at one, two, and three hours after induction. Portions of these cultures representing equal numbers of cells were then lysed and analyzed by SDS-PAGE. The amount of fusion protein produced in cells harboring the rop⁻ version of the expression plasmid was two to three times greater than that from cells containing the parent plasmid, based on the intensity of staining of 12% SDS-PAGE analytical gel by Coomassie blue, at all induced time points.

EXAMPLE 12

Chemical Amidation of Unprotected Peptide MSI-344 (SEQ ID NO: 4)

The unprotected MSI-344 peptide (SEQ ID NO: 4), i.e., having unmodified α-amino group and the ε-amino groups of lysine residues, was first converted to the methyl ester following a general approach for converting amino acids to their methyl esters as described by Brenner and Huber [Brenner, M. and Huber, W. (1953) Helv. Chim. Acta 36, 1109]. Briefly 80 μL of thionyl chloride was added to 500 μL of absolute methanol, cooled on ice, and stirred for about 15 min. To this solution was added 25 mg of the MSI-344 peptide (SEQ ID NO: 4) and the solution was stirred overnight at room temperature. Solvent was removed and the residue was lyophilized from water to obtain the hydrochloride salt of the peptide methyl ester. The conversion of the methyl ester to the amide was then achieved by reacting it with ammonia following standard procedures of organic synthesis. In the present description of the invention, the unprotected peptide methyl ester was directly converted to the amide. Briefly, 25 mL of absolute methanol was saturated with dry ammonia gas and the peptide methyl ester was added to that solution and stirred in a sealed flask for several days (2–5 days). After removing excess ammonia and methanol, the desired product peptide MSI-78 $NH_2$-GIGK-FLKKAKKFGKAFVKILKK-$NH_2$ (SEQ ID NO: 51) was obtained after lyophilizing it from water. The MSI-78 peptide (SEQ ID NO: 51) thus obtained was dissolved in 0.1% trifluoroacetic acid in water, and was characterized by coeluting it with a chemically-synthesized MSI-78 peptide (SEQ ID NO: 51) on HPLC, and also by determining its mass spectrum, elemental analysis and sample biological activity. The one major by-product detected by HPLC was identified as a cyclic lactam by mass spectral measurement.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for recombinantly producing an antimicrobial amphiphilic, ion channel-forming peptide, comprising:
    a. providing a protease-deficient microbial host transformed with an expression vector having DNA that encodes the peptide as a fusion protein under the control of a regulatory sequence operable in the microbial host; and
    b. expressing the peptide as a fusion protein in the transformed microbial host, wherein the peptide is expressed in soluble form.

2. The method of claim 1, wherein the peptide is expressed as a cleavable fusion protein and the method further comprises cleaving the fusion protein to obtain the peptide.

3. A method for recombinantly producing an antimicrobial, amphiphilic, ion channel-forming peptide, comprising:
    a. providing an *E. coli* protease-deficient K-12 cell transformed with a vector that expresses a cleavable fusion protein comprising at least part of a carbohydrate binding protein and the peptide in the cell;
    b. expressing the fusion protein in the cell; and
    c. cleaving the fusion protein to obtain the peptide substantially free of carbohydrate binding protein residues.

4. The method of claim 1 or 3 wherein the peptide is selected from the group consisting of:
    a. a magainin peptide;
    b. a cecropin;
    c. a sarcotoxin;
    d. an XPF peptide;
    e. a PGLa peptide;
    f. a CPF peptide;
    g. a melittin;
    h. an apidaecin;
    i. a tachyplesin,
    j. a polyphemusin, and
    k. analogs thereof.

5. The method of claim 1 or 3 wherein the peptide is selected from the group consisting of:
    a. SEQ ID NO: 1;

b. SEQ ID NO: 2;
c. SEQ ID NO: 3;
d. SEQ ID NO: 4;
e. SEQ ID NO: 5;
f. SEQ ID NO: 6;
g. SEQ ID NO: 7;
h. SEQ ID NO: 8;
i. SEQ ID NO: 9;
j. SEQ ID NO: 10; and
k. SEQ ID NO: 11.

6. The method of claim 1 or 3 wherein the DNA encoding the peptide encodes two or more amphiphilic peptides.

7. The method of claim 6 wherein the DNA encoding one amphiphilic peptide is joined to the DNA of at least one other amphiphilic peptide by a DNA segment unrelated to any of the amphiphilic peptide coding sequences.

8. The method of claim 1 or 3 wherein the expression vector containing the DNA insert is selected from the group consisting of:
a. pMALc344;
b. pMALc344(rop⁻);
c. pMALc556;
d. pLim1;
e. pP1; and
f. pMag2.

9. The method of claim 1 or 3 wherein the expression vector is a rop⁻ derivative of a ColE1 replicon.

10. The method of claim 9 wherein the ColE1 replicon is pBR322.

11. The method of claim 3 wherein the carbohydrate binding protein is a maltose binding protein.

12. The method of claim 11 wherein the maltose binding protein is the *E. coli* malE gene product.

13. The method of claim 12 wherein the *E. coli* malE gene product comprises the first 121 amino acids of the gene product.

14. The method of claim 12 wherein the *E. coli* malE gene product is produced by the pMAL-c2 vector.

15. The method of claim 3 wherein the carbohydrate binding protein is B-chain toxin of ricin.

16. The method of claim 3 wherein the *E. coli* protease-deficient K-12 strain is an ompT⁻ strain.

17. The method of claim 16 wherein the ompT⁻ strain is the strain UT400.

18. The method of claim 16 wherein the ompT⁻ strain is the strain UT5600.

19. The method of claim 16 wherein the transformed *E. coli* strain is selected from the group consisting of:
a. pMALc344/UT400;
b. pMALc344/UT5600;
c. pMALc556/UT400;
d. pMALc556/UT5600;
e. pLim1/UT400;
f. pP1/UT400; and
g. pMag2/UT400.

20. The method of claim 3 wherein the *E. coli* protease-deficient K-12 strain displays a lon⁻ genotype.

21. The method of claim 20 wherein the lon⁻ strain is PR745.

22. The method of claim 3 wherein the portion of a carbohydrate binding protein is sufficient to allow binding of the fusion protein to a carbohydrate affinity matrix.

23. The method of claim 22 further comprising, prior to cleavage of the fusion protein, the steps of:
a. binding the fusion protein to a carbohydrate affinity matrix in a buffered salt solution maintained at a pH in the range 7–9;
b. washing the column with the buffered salt solution maintained at a pH in the range 7–9; and
c. eluting the fusion protein in the buffered salt solution maintained at a pH in the range 7–9 and containing unbound and soluble carbohydrate at a concentration sufficient to displace the fusion protein.

24. The method of claim 3 wherein the fusion protein is cleaved with an enzyme.

25. The method of claim 24 wherein the enzyme is factor Xa.

26. The method of claim 3 wherein the fusion protein is cleaved by incubating the fusion protein in a suitable buffered aqueous solution with a cleavage chemical mixture.

27. The method of claim 26 wherein the cleavage chemical mixture contains cyanogen bromide.

28. The method of claim 26 wherein the aqueous buffered solution contains an acid selected from the group comprising:
a. hydrochloric acid;
b. formic acid; and
c. trifluoroacetic acid.

29. The method of claim 28 wherein the acid is hydrochloric acid at a concentration in the range of 0.1–0.2M.

30. The method of claim 28 wherein the acid is formic acid at a concentration of about 70% in water.

31. The method of claim 28 wherein the acid is trifluoroacetic acid at a concentration of about 70% in water.

32. The method of claim 26 wherein the cleavage chemical mixture contains hydroxylamine.

33. The method of claim 26 wherein the cleavage chemical mixture is a mixture of two chemicals each at a concentration sufficient for cleaving peptide bonds.

34. The method of claim 33 wherein the cleavage chemical mixture contains hydroxylamine and 2-nitro-5-thiocyano-benzoic acid.

35. The method of claim 3 further comprising, after cleaving, the additional step of C-terminal amidation of the peptide by chemical or enzymatic reagents.

36. The method of claim 35 wherein C-terminal amidation is achieved with an enzymatic reagent.

37. The method of claim 36 wherein the enzymatic reagent is a peptidyl-glycine α-amidating monooxygenase.

38. The method of claim 37 wherein the peptidyl-glycine α-amidating monooxygenase is isolated from rat medullary thyroid cells.

39. The method of claim 35 wherein C-terminal amidation is achieved by treatment of the peptide with chemical reagents in steps comprising:
a. esterification of the peptide in an anhydrous methanol-thionyl chloride mixture; and
b. conversion of the peptide methyl ester to a peptide amide in a reagent selected from the group consisting of:
(1) anhydrous methanolic ammonia; and
(2) liquid ammonia.

* * * * *

UNITED STATES PATENT AND TRADEMARK OFFICE
CERTIFICATE OF CORRECTION

PATENT NO. : 5,589,364

DATED : December 31, 1996

INVENTOR(S) : Williams et al.

It is certified that error appears in the above-identified patent and that said Letters Patent is hereby corrected as shown below:

At cols. 9 and 10, on the table following line 29, the amino acid sequence for MSI-556 (SEQ ID NO:6) should read --NH₂-GIGKFLKKAKKFGKAFVKILKKG-OH--.

At cols. 47 and 48, the last line should read --Gly Ile Gly Lys Phe Leu Lys Lys Ala Lys Lys Phe Gly Lys Ala Phe --

Signed and Sealed this

Third Day of August, 1999

Attest:

Q. TODD DICKINSON

Attesting Officer

Acting Commissioner of Patents and Trademarks